United States Patent [19] [11] Patent Number: 4,548,815
Ponsford et al. [45] Date of Patent: Oct. 22, 1985

[54] ANTIBACTERIAL AGENTS

[75] Inventors: Roger J. Ponsford, Horsham; Thomas T. Howarth, Cranleigh, both of England

[73] Assignee: Beecham Group p.l.c., England

[21] Appl. No.: 538,767

[22] Filed: Oct. 3, 1983

Related U.S. Application Data

[60] Division of Ser. No. 278,564, Jun. 29, 1981, , which is a continuation of Ser. No. 786,345, Apr. 11, 1977, abandoned, which is a continuation-in-part of Ser. No. 730,475, Oct. 7, 1976, abandoned.

[30] Foreign Application Priority Data

Oct. 13, 1975 [GB] United Kingdom .............. 41897/75
Jan. 23, 1976 [GB] United Kingdom .............. 02629/76
May 8, 1976 [GB] United Kingdom .............. 19000/76
Nov. 27, 1976 [GB] United Kingdom .............. 49570/76
Nov. 27, 1976 [GB] United Kingdom .............. 49569/76
Dec. 11, 1976 [GB] United Kingdom .............. 51808/76
Mar. 10, 1977 [GB] United Kingdom .............. 10116/77
Mar. 16, 1977 [GB] United Kingdom .............. 11116/77

[51] Int. Cl.$^4$ ............................................ A61K 35/00
[52] U.S. Cl. .................................................. 424/114
[58] Field of Search ........................................ 424/114

Primary Examiner—Jerome D. Goldberg
Attorney, Agent, or Firm—Jacobs & Jacobs

[57] ABSTRACT

The compounds of the formula (II):

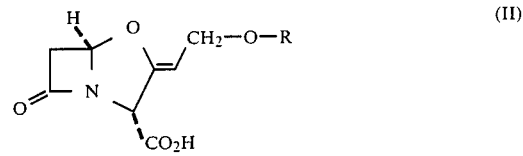

and salts and esters thereof wherein R is an inert ogranic group of up to 18 carbon atoms and are able to inhibit the action of various bacterial β-lactamases. Thus when a compound of the formula (II) or its salt or ester is used together with a penicillin or cephalosporin, the effectiveness of that penicillin or cephalosporin can be considerably enhanced. These novel synergysts can be prepared by etherification of an ester of clavulanic acid followed if desired by deesterification. The novel synergysts also possess antibacterial activity.

48 Claims, No Drawings

ANTIBACTERIAL AGENTS

CROSS-REFERENCE

This is a division of Ser. No. 278,564 filed June 29, 1981 which is a continuation of Ser. No. 786,345 now abandoned filed Apr. 11, 1977, which itself is a CIP of Ser. No. 730,475 now abandoned filed Oct. 7, 1976.

BACKGROUND OF THE INVENTION

Belgian Pat. No. 827926 discloses inter alia clavulanic acid and its salts and esters which substance clavulanic acid has the formula (I):

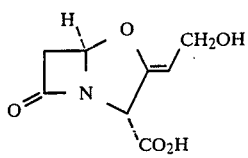

Clavulanic acid and its salts and esters are able to inhibit β-lactamases from a range of bacteria and owing to this useful property are able to enhance the effectiveness of penicillins and cephalosporins against many gram-positive and gram-negative bacteria.

DESCRIPTION OF THE INVENTION

It has now been discovered that certain derivatives of clavulanic acid also possess anti-bacterial and β-lactamase inhibitory activity. The activity of these novel compounds differs from that of the known compounds and so offers the physician a choice of medicaments. Furthermore the preferred novel compounds have improved blood levels and can lead to improved effectiveness in-vivo.

The present invention provides ethers of the formula (II):

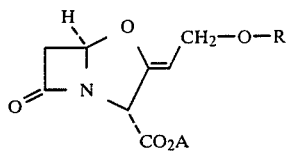

wherein R is an inert organic group of up to 18 carbon atoms and A is a group such that $CO_2A$ represents a carboxylic acid group or a salt or ester thereof.

One sub-group of compounds of the formula (II) of note is that of the formula (IIa):

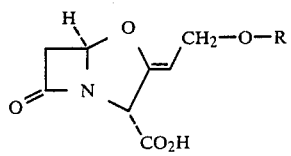

and its salts (especially pharmaceutically acceptable salts) wherein R is as defined in relation to formula (II).

A further sub-group of compounds of the formula (II) of note is that of the formula (IIb):

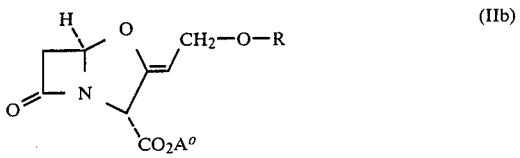

wherein $A°$ is a group such that $CO_2A°$ is an ester and R is as defined in relation to formula (II).

Most suitably R contains up to 7 carbon atoms.

Suitable inert organic groups R for inclusion in the compounds of the formulae (II), (IIa) and (IIb) include hydrocarbon groups and hydrocarbon groups inertly substituted by halogen, ether, acyloxy, acyl, ester, carboxyl or salted carboxyl, hydroxyl, nitro, cyano, amino and substituted amino and the like so that suitable groups R include hydrocarbon and hydrocarbon substituted by halogen and/or groups of the sub-formulae $OR^1$, OH, $OCOR^1$, $CO.R^1$, $CO_2R^1$, $NR^2.CO.R^1$, $NR^2.CO_2R^1$, $SOR^1$, $SO_2R^1$, $NH_2$, $NR^1R^2$, $NO_2$, CN or $CO.NR^1R^2$ wherein $R^1$ is a hydrocarbon group of up to 8 carbon atoms and $R^2$ is a hydrocarbon group of up to 4 carbon atoms.

When used herein the term "hydrocarbon" includes alkyl, alkenyl and alkynyl groups and such groups substituted by phenyl or hydrocarbon substituted phenyl groups and the like.

Suitable inert organic groups R for inclusion in the compounds of the formulae (II), (IIa) and (IIb) include hydrocarbon groups and hydrocarbon groups inertly substituted by halogen and/or groups of the sub formulae $OR^1$, $O.COR^1$, $CO.R^1$, $CO_2R^1$ wherein $R^1$ is a hydrocarbon group of up to 8 carbon atoms.

Most suitably $R^1$ is an alkyl group of 1-4 carbon atoms or a phenyl or benzyl group. A preferred group $R^1$ is the methyl group. A preferred group $R^2$ is the methyl group.

A further suitable sub-group of compounds of the formulae (II), (IIa) and (IIb) are those wherein R is a group $CR^4R^5R^6$ wherein $R^4$ and $R^5$ are independently alkyl groups of up to 3 carbon atoms or a phenyl group optionally substituted by halogen or a group of the formula $R^7$ or $OR^7$ where $R^7$ is an alkyl group of up to 3 carbon atoms; and $R^6$ is a hydrogen atom or an alkyl group of up to 3 carbon atoms or a phenyl group optionally substituted by halogen or a group of the formula $R^8$ or $OR^8$ where $R^8$ is an alkyl group of up to 3 carbon atoms.

Certain particularly suitable compounds of the formulae (II), (IIa) and (IIb) possessing intrinsically good activity against certain β-lactamase producing strains of *Staphylococcus aureus* include those wherein R is group $CH_2R^9$ wherein $R^9$ is a naphthyl, phenyl or phenyl group substituted by halogen or a group $R^{10}$ or $OR^{10}$ where $R^{10}$ is an alkyl group of up to 3 carbon atoms.

When used herein the term "inertly substituted" means that inclusion of the substituent does not produce an inherently unstable compound which cannot be used as a medicinal agent.

Suitable groups A for inclusion in the compounds of the formula (II) include hydrogen and salting ions such as lithium, sodium, potassium, calcium, magnesium, ammonium and conventional substituted ammonium ions such as monoalkylamines, dialkylamines, trialkylamines (such as trimethyl or triethylammonium), quaternary alkylamines and the like.

Favoured salts of the compounds of the formula (II) include the lithium, sodium, potassium, and calcium salts.

Particularly suitable salts of this invention include the compounds of the formula (II) wherein A represents a lithium, sodium or potassium ion, especially sodium or potassium and preferably sodium.

Suitable esters of the compounds of the formula (II) include those of the formulae (III) and (IV):

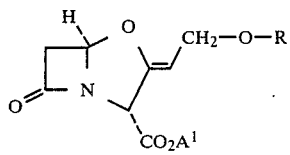
(III)

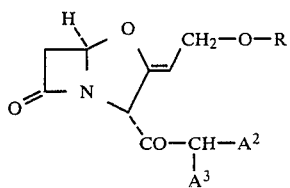
(IV)

wherein R is as defined in relation to formula (II) and $A^1$ is an alkyl group of 1-8 carbon atoms optionally substituted by halogen or a group of the formula $OA^4$, $OCOA^4$, $SA^4$, $SO_2A^4$ wherein $A^4$ is a hydrocarbon group of up to 6 carbon atoms; $A^2$ is a hydrogen atom, an alkyl group of up to 4 carbon atoms or a phenyl group optionally substituted by halogen or by a group $A^5$ or $OA^5$ where $A^5$ is an alkyl group of up to 6 carbon atoms; and $A^3$ is a phenyl group optionally substituted by halogen or by a group $A^5$ or $OA^5$ where $A^5$ is an alkyl group.

Most suitably $A^1$ is an alkyl group of 1-8 carbon atoms optionally substituted by a group of the formula $OA^4$ where $A^4$ is a hydrocarbon group of up to 6 carbon atoms. Preferably $A^1$ is a straight chained alkyl group. Preferably $A^4$ is a methyl group. Most suitably $A^2$ is a hydrogen atom. Most suitably $A^5$ is a methyl group. $A^1$ may also with advantage be an alkenyl group of 3-6 carbon atoms, for example an allyl group.

Esters of this invention are preferably in-vivo hydrolysable. Suitable esters include those described in Belgian Pat. No. 827926 (which has the same disclosure in this respect to U.S. Ser. No. 569007) as being in-vivo hydrolysable when attached to clavulanic acid. Particularly suitable in-vivo hydrolysable esters include acetoxymethyl, α-acetoxyethyl, pivaloyloxymethyl, phthalidyl, ethoxycarbonyloxymethyl, ethoxycarbonyloxyethyl and the like.

Benzyl esters of the compounds of the formula (II) are particularly useful hydrogenolysable esters. Other particularly useful hydrogenolysable esters include the p-methoxybenzyl esters.

The preceding ester moieties are also suitable for incorporation into the compounds of the formulae (V)—(IX) as hereinafter described.

A further particularly suitable group of compounds of this invention is that of the formula (V):

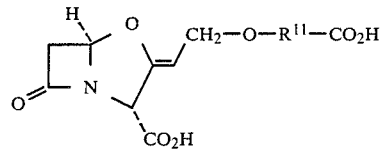
(V)

and salts and esters thereof wherein $R^{11}$ is a hydrocarbon group of 1-8 carbon atoms optionally inertly substituted by halogen and/or $OR^{12}$, $OCOR^{12}$, $CO.R^{12}$ or OH group where $R^{12}$ is an alkyl group of 1-4 carbon atoms.

Most suitably $R^{11}$ is an alkylene group of 1-4 carbon atoms, a phenylene group or an alkylene group of 1-4 carbon atoms substituted by a phenyl or phenylene group.

Preferably $R^{11}$ is an alkylene group of 1-4 carbon atoms such as the $-CH_2-$ or $-CH_2.CH_2-$ groups.

A particularly suitable group of compounds of the formula (V) are those of the formula (VI):

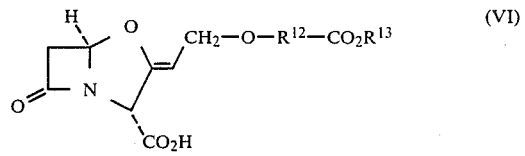
(VI)

and salts and esters thereof wherein $R^{12}$ is an alkylene group of 1-4 carbon atoms and $R^{13}$ is a hydrogen atom or an alkyl group of 1-4 carbon atoms or an alkyl group of 1-4 carbon atoms substituted by a phenyl group.

Preferably $R^{12}$ is a $-CH_2-$ or $-CH_2.CH_2-$ group.

Most suitably the compounds of the formula (VI) are in the form of a pharmaceutically acceptable salt.

A further particularly suitable group of compounds of this invention is that of the formula (VII):

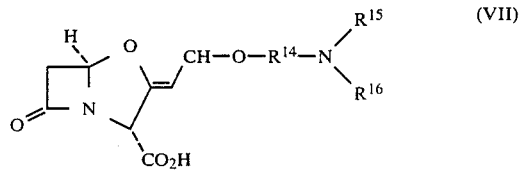
(VII)

and salts and esters thereof wherein $R^{14}$ is a divalent hydrocarbon group of 2-8 carbon atoms; $R^{15}$ is a hydrogen atom or an alkyl group of 1-4 carbon atoms and $R^{16}$ is a hydrogen atom or a $R^{17}$, $CO.R^{17}$ or $CO_2R^{17}$ group where $R^{17}$ is an alkyl group of 1-4 carbon atoms optionally substituted by a phenyl group.

Most suitably $R^{14}$ is an alkylene group of 2-4 carbon atoms, a phenylene group or an alkylene group of 2-4 carbon atoms substituted by a phenyl or phenylene group.

A further particularly suitable group of compounds of this invention are those of the formula (VIII):

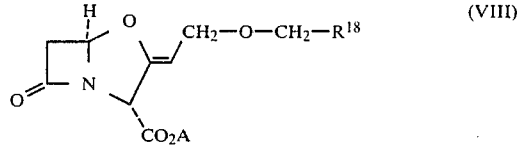
(VIII)

wherein A is as defined in relation to formula (II) and $R^{18}$ is a group such that $CH_2R^{18}$ is a group R as defined in relation to formula (II).

Particularly suitable compounds of the formula (VIII) include salts and esters of the types hereinbefore described.

Certain favoured compounds of the formula (VIII) include those of the formula (IX):

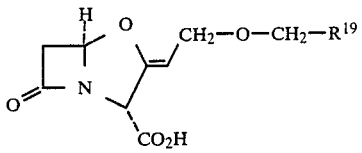

(IX)

and pharmaceutically acceptable salts thereof wherein $R^{19}$ is an alkyl group of 1-4 carbon atoms or a phenyl group or one of the aforenamed groups substituted by a carboxylic acid group or a salt or $C_{1-4}$ alkyl ester or $R^{19}$ is a carboxylic acid group or a salt or $C_{1-4}$ alkyl ester thereof.

Esters of the compounds of the formula (IX) are also favoured compounds of this invention especially when hydrolysable in-vivo.

Salts of this invention are useful as intermediates in preparing corresponding esters or in preparing other salts.

Thus in a favoured aspect this invention provides salts of the compounds of the formula (II), (V), (VI), (VII), (VIII) and (IX) as hereinbefore defined.

Suitable salts used as intermediates include alkali metal salts such as the lithium, sodium or potassium salts; alkaline earth metal salts such as the magnesium, calcium and barium salts; the ammonium salt and substituted ammonium salts such as trialkylamine salts such as the triethylamine salt; or other salts which have been disclosed as being suitable salts of clavulanic acid.

The lithium salts of the ethers of this invention are a favoured aspect of this invention.

The sodium salts of the ethers of this invention are a further favoured aspect of this invention.

The potassium salts of the ethers of this invention are another favoured aspect of this invention.

The calcium salts of the ethers of this invention are also a favoured aspect of this invention.

Preferably the salts of this invention are crystalline. Some crystalline salts contain water of hydration.

Certain highly favoured compounds of this invention include the salts (especially the pharmaceutically acceptable salts) of the compound of the formula (X):

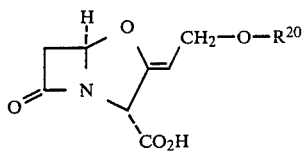

(X)

wherein $R^{20}$ is an alkyl group of 1-5 carbon atoms.

Suitably $R^{20}$ is a group $CH_2R^{21}$ wherein $R^{21}$ is an alkyl group of 1-4 carbon atoms or a hydrogen atom.

Suitable groups $R^{21}$ include the methyl, ethyl, n-propyl, iso-propyl, n-butyl, iso-butyl, sec-butyl and t-butyl groups.

Preferred groups $R^{20}$ include the methyl and ethyl groups, the methyl group being particularly preferred.

Other highly favoured compounds of this invention include esters of the compounds of the formula (IX). Particularly suitable esters of the compounds of the formula (X) include those of the formula (XIa) and (XIb):

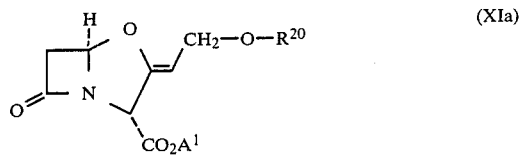

(XIa)

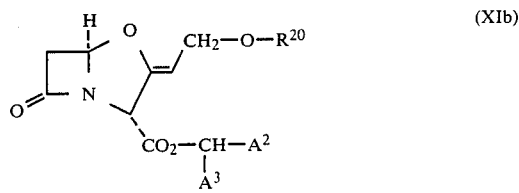

(XIb)

wherein $A^1$, $A^2$ and $A^3$ are as defined in relation to formula (III) and (IV). Suitably the groups $R^{20}$ are as described in relation to the compounds of the formula (X). Suitably the groups $A^2$ and $A^3$ are as described in relation to the compound of the formula (IV). Such compounds may be converted into the compounds of the formula (X) by hydrogenation in the presence of an appropriate base.

A further group of highly suitable compounds of this invention are the methoxymethyl esters of the compounds of the formula (X). Such compounds may be converted into the compounds of the formula (X) by mild basic hydrolysis.

Other suitable esters are these described in Belgian Pat. No. 827926 as being in-vivo hydrolysable when attached to clavulanic acid. Particularly suitable in-vivo hydrolysable esters are believed to include acetoxymethyl, α-acetoxyethyl, pivaloyloxymethyl, phthalidyl, ethoxycarbonyloxymethyl, α-ethoxycarbonyloxyethyl and the like.

The lithium salts of the compounds of the formula (X) are useful for preparing the sodium, potassium, calcium and like salts by ion-exchange for example by using a salted carboxy-substituted polyvinylbenzene resin.

The sodium salts of the compounds of the formula (X) are particularly suitable for use in injectable pharmaceutical compositions.

The sodium, potassium and calcium salts of the compounds of the formula (X) are particularly suitable for use in orally administrable pharmaceutical compositions.

The present invention also provides pharmaceutical compositions which comprise a compound of this invention and a pharmaceutically acceptable carrier.

The compositions of this invention include those in a form adapted for oral, topical or parenteral use and may be used for the treatment of infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrants and the like in accordance with conventional pharmaceutical practice in the manner well understood by those skilled in the art of formulating antibiotics.

Injectable or infusable compositions of salts of a compound of the formula (II) are particularly suitable as high tissue levels of a compound of the formula (II) can occur after administration by injection or infusion. Thus, one preferred composition aspect of this invention comprises a salt of a compound of the formula (II) in sterile form.

Unit dose compositions comprising a compound of the formula (II) or a salt or ester thereof adapted for oral administration form a further preferred composition aspect of this invention.

The compound of the formula (II) or its salt or ester may be present in the composition as sole therapeutic agent or it may be present together with other therapeutic agents such as β-lactam antibiotic. Suitable β-lactam antibiotics for inclusion in the compositions of this invention include benzylpenicillin, phenoxymethylpenicillin, carbenicillin, azidocillin, propicillin, ampicillin, amoxycillin, epicillin, ticarcillin, cyclacillin, cefatriazine, pirbenicilllin, α-sulphonyloxybenzylpenicillin, cephaloridine, cephalothin, cefazolin, cephalexin, cefoxitin, cephacetrile, cephamandole nafate, cephapirin, cephradine, 4-hydroxycephalexin, cefaparole, cephaloglycine, and other well known penicillins and cephalosporins or pro-drugs therefore such as hetacillin, metampicillin, 4-acetoxyampicillin, the acetoxymethyl, ethoxycarbonyloxymethyl, pivaloyloxymethyl or phthalidyl esters of benzylpenicillin, ampicillin, amoxycillin, or cephaloglycine or the phenyl, tolyl or indanyl α-esters of carbenicillin or ticarcillin or the like: or perbenicillin, cefetriazine, azclocillin, mezlocillin or the like. Such compounds are frequently used in the form of a salt or hydrate.

Naturally if the penicillin or cephalosporin present in the composition is not suitable for oral administration then the composition will be adapted for parenteral administration.

When present in pharmaceutical composition together with a β-lactam antibiotic, the ratio of a compound of the formula (II) or its salt or ester present to β-lactam antibiotic present may vary over a wide range of ratios, for example 10:1 to 1:10 for example 3:1 to 1:3. Thus ratios of antibiotic to synergist include 10:1, 5:1, 4:1, 3:1, 2:1, 1:1, 1:2, 1:3, 1:5, 1:10 and the like. Normally smaller quantities of synergist than penicillin or cephalosporin are employed.

The total quantity of antibacterial agents present in any unit dosage form will normally be between 50 and 1500 mg and will usually be between 100 and 1000 mg.

Compositions of this invention may be used for the treatment of infections on inter alia, the respiratory tract, the urinary tract and soft tissues and mastitis in cattle.

Normally between 50 and 3000 mg of the compounds of the invention will be administered each day of treatment but more usually between 100 and 1000 mg of the compounds of the invention will be administered per day, for example as 1-6 doses, more usually 2-4 doses.

The penicillin or cephalosporin in synergistic compositions of this invention will normally be present by up to or at approximately the amount at which it is conventionally used.

Particularly favoured compositions of this invention will contain from 150-1000 mg of amoxycillin, ampicillin or a pro-drug therefore and from 50-500 mg of a compound of the formula (II) or a salt or in-vivo hydrolysable ester thereof and more suitably from 200-500 mg of amoxycillin, ampicillin or a pro-drug therefore and from 50-250 mg of a compound of the formula (II) or a salt or in-vivo hydrolysable ester thereof.

Most suitably the compound of the formula (II) is in the form of a pharmaceutically acceptable salt. Most suitably the pencillin is zwitterionic or the form of a sodium or potassium salt.

The materials present in such compositions may be hydrated if required, for example ampicillin trihydrate or amoxycillin trihydrate may be employed. The weights of the antibiotics in such compositions are expressed on the basis of antibiotic theoretically available from the composition and not on the basis of the weight of pro-drug.

Certain preferred compositions of this invention will contain the pharmaceutically acceptable salts of the compounds of the formula (X) as hereinbefore defined. For example the sodium salts of the compounds of the formula (X) may be included in injectable compositions and the sodium, potassium or calcium salts and the like may be included in compositions for oral administration. Lithium salts may be used for low dose orally administrable compositions.

Administration of such compositions, for example of salts of the methyl or ethyl ethers can lead to favourable blood levels after administration; for example administration of a salt of the methyl ether in test mammals leads to a more prolonged blood level than an equivalent amount of the salt of clavulanic acid.

The present invention provides a process for the preparation of a compound of the formula (II) as hereinbefore defined which process comprises the etherification of an ester of clavulanic acid and thereafter if desired replacing the ester group by a carboxylic acid group or a salt or alternative ester thereof by methods known per se.

Normally the etherification reaction takes place on an ester of clavulanic acid which is readily hydrogenolysable to the parent acid, for example the benzyl ester or its chemical equivalent.

Esters within formula (II) may be prepared by the reaction of an alcohol of the formula (XII):

R—OH    (XII)

wherein R is as defined in relation to formula (II) with the corresponding ester of a compound of the formula (I) in the presence of a Lewis acid catalyst such as boron trifluoride or its equivalent such as a boron trifluoride etherate, for example $BF_3.O(C_2H_5)_2$.

The preceding reaction normally takes place in a solvent inert under the reaction conditions such as chloroform, dichlormethane, tetrahydrofuran or dioxane at a depressed or non-elevated temperature, for example −80° C. to +30° C., and preferably at a depressed temperature, for example −50° C. to 0° C., and conveniently at about −30° C.

An alternative form of this method of preparation of esters within the formula (II) comprises the reaction of an alcohol of the formula (XII):

R—OH    (XII)

wherein R is as defined in relation to formula (II) with the corresponding ester of clavulanic acid wherein the hydroxyl group is masked so that the compound is of the formula (XIII):

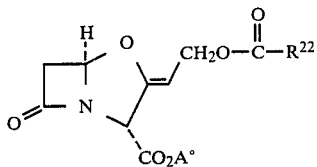

(XIII)

wherein $R^{22}$ is a $C_{1-6}$ alkyl group optionally inertly substituted by one or more halogen atoms and $CO_2A°$ is an ester group in the presence of a Lewis acid.

The conditions for this reaction are similar to those outlined above for the reaction of the compound of formula (X) with an ester of the compound of the formula (I).

The compounds of the formula (XIII) may be prepared as described in Belgian Pat. No. 834645, that is by the reaction of a compound of the formula:

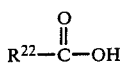

or a reactive acylating derivative thereof with the corresponding ester of clavulanic acid.

The preceding methods do not generally give such acceptable yields as the methods hereinafter described.

Esters within the formula (II) wherein R is a group of the formula $CH_2R^{18}$ wherein $R^{18}$ is a residue of the group R may be prepared by the reaction of the corresponding ester of clavulanic acid with a diazolkane of the formula $N_2$—$CHR^{18}$.

Most suitably this reaction takes place in the presence of boron trifluoride.

Such reactions will take place in an inert solvent such as tetrahydrofuran or the like at a non-extreme temperature such as $-30°$ C. to $22°$ C.

The preferred method of preparing esters within the formula (II) comprises the reaction of the corresponding ester of clavulanic acid with a compound of the formula (XIV):

$$N_2R^{23} \qquad (XIV)$$

wherein $R^{23}$ is a group within the definition of R which is unreactive towards diazocompounds.

Suitable groups $R^{23}$ include alkyl, alkenyl, aryl or aralkyl groups of up to 18 carbon atoms inertly substituted, for example by halogen. Particularly suitable groups include hydrocarbon groups of up to 18 carbon atoms, for example alkyl groups such as those of up to 7 carbon atoms.

Preferred groups $R^{23}$ are of the formula $CH_2R^{24}$ where $R^{24}$ is the residue of the $R^{23}$ group. Other particularly suitable groups $R^{23}$ are those which result in the production of particularly suitable compounds as hereinbefore described.

Most suitably and normally the preceding reaction takes place in the presence of a Lewis acid catalyst.

The preferred Lewis acid catalyst is boron trifluoride or its equivalent such as a boron trifluoride etherate, for example, $BF_3.O(C_2H_5)_2$.

The preceding reaction normally takes place in a solvent inert under the reaction conditions such as chloroform, dichloromethane, tetrahydrofuran, dioxane or the like.

Most suitably the reaction takes place at a depressed or non-elevated temperature, for example $-80°$ C. to $+30°$ C., and preferably at a depressed temperature, for example $-30°$ C. to $+10°$ C. We have found a convenient suitable temperature for carrying out the reaction to be about $-20°$ C. to $0°$ C.

Salts within formula (II) may be prepared from esters within formula (II) by very mild basic hydrolysis, for example by hydrolysis in an aqueous solution maintained at pH 7 to 9 by the slow addition of base.

Acids and salts within formula (II) may be prepared from hydrogenolysable esters within formula (II) by hydrogenation using a medium or low pressure of hydrogen in the presence of a transition metal catalyst.

Palladium, for example 10% palladium on charcoal, has proved a particularly useful catalyst. We have found that a suitable weight ratio for the weight of 10% palladium on charcoal used to the weight of ether used is 1:3.

The hydrogenation reaction preferably occurs in a solution in a solvent which consists of or contains tetrahydrofuran.

Suitable hydrogenolysable esters include those of the formula (IV) as hereinbefore defined. Preferred hydrogenolysable esters includes the benzyl ester and the p-methoxybenzyl esters.

The products may be purified chromatographically if desired in conventional manner.

If a base such as sodium hydrogen carbonate, potassium hydrogen carbonate, lithium carbonate, calcium carbonate or the like is included in the reaction mixture then the resulting compound is in the form of a salt. If no such base is included the product is in the form of the free acid.

Salts within formula (II) may also be prepared by cation exchange, for example a lithium salt may be converted into a sodium, potassium, calcium or other salt in conventional manner such as by applying a solution of the lithium salt to an ion exchange resin in the sodium, potassium, calcium or other salt form.

Acids within formula (II) may also be prepared by the careful acidification of the corresponding sodium or like salt. The thus formed acid may then be extracted into water immiscible organic solvent from which it may be recovered by evaporation.

From the preceding comments it will be appreciated that this invention provides a process for the preparation of the compounds of the formula (II) wherein $CO_2A$ is a carboxylic acid or a salt thereof which process comprises the deesterification of a corresponding compound of the formula (II) wherein $CO_2A$ is an ester group.

Those compounds of the formula (II) which contain a relatively reactive moiety such as an amino, carboxylic acid or hydroxyl group may be prepared by the previously described processes if the moiety is protected during the condensation reaction.

Suitable protecting groups include benzyloxycarbonyl derivatives for amino or hydroxyl groups and benzyl esters for the carboxyl group. Such protecting groups may be removed by hydrogenation in conventional manner.

Esters within the formula (II) may be prepared by the reaction of a corresponding salt such as an alkali metal salt within the formula (II) (most suitably a sodium salt) with an esterifying agent such as a halide or active ester such as a chloride, bromide, iodide, methane sulphonate, toluene sulphonate or the like or by reaction of an acid within formula (II) with a diazo compound or an alcohol in the presence of dicyclohexylcarbodiimide. Such reactions proceed under conventional conditions.

Thus the present invention provides a process for the preparation of the compounds of the formula (II) wherein $CO_2A$ is an ester group which process comprises the esterification of the corresponding compound of the formula (II) wherein $CO_2A$ is a carboxylic acid group or a salt thereof.

Normally and preferably the processes of this invention are adapted to prepare those compounds of the formulae (II)–(X) as hereinbefore described as being preferred compounds of this invention.

The esters within the formula (II) may also be prepared by the etherification of the corresponding ester of clavulanic acid by reaction with a compound of the formula (XV):

Q—R  (XV)

wherein Q is a group readily displaceable by an electron rich moiety.

Suitably Q is a chlorine, bromine or iodine atom or an active ester such as a methane sulphone, toluene sulphonate or their chemical equivalent. Most suitably Q—R is a group of the formula Q—$CH_2R^{18}$ where $R^{18}$ is as hereinbefore defined.

Normally the reaction is carried out in the presence of an acid acceptor such as collidine, dicyclohenylamine or the like.

This invention also provides a process for the preparation of a compound of the formula (XVI):

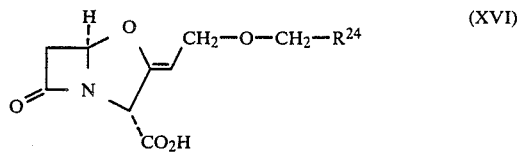

and salts and esters thereof wherein $R^{24}$ is hydrogen atom or a phenyl group or a $R^{21}$ group as defined in relation to formula (X); which process comprises the reaction of an ester of the compound of the formula (I):

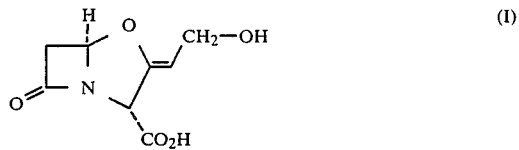

with a compound of the formula (XVII)

$(R^{24}CH_2)_3O^{\oplus}BF_4^{\ominus}$  (XVII)

wherein $R^{24}$ is as defined in relation to formula (XVI) and thereafter if desired forming the free acid or a salt thereof from the ester.

The etherification reaction is carried out in a dry non-hydroxylic solvent such as dichloromethane, chloroform, carbon tetrachloride, or other haloalkane or the like.

Normally the etherification takes place at a temperature of from −60° C. to 60° C., more usually from −40° C. to 30° C., for example from about 0° to about 20° C. Ofen it is convenient to start the reaction at a depressed temperature and to allow it to increase gradually to approximately ambient temperature.

Preferably the etherification takes place in the presence of a base. Most suitably the base is a carbonate or bicarbonate such as sodium carbonate, sodium bicarbonate, lithium carbonate, potassium carbonate, calcium carbonate or the like.

Once the etherification is substantially complete (for example as shown by thin layer chromatography) the desired compound may be obtained from the reaction mixture by washing with water to remove ionic materials and then drying and evaporating the organic phase and if desired further purifying the ether by chromatography.

The preceding process may be adapted to produce esters of the compound of the formula (XVI) where $R^{24}$ is hydrogen atom or a phenyl, methyl, ethyl, n-propyl, n-butyl or the like. Preferred compounds which can be prepared include those wherein R is a hydrogen atom or a methyl group.

Esters of the compounds of the formula (XVI) may be converted to the free acid or its salts by the methods described hereinbefore. Such methods include the hydrogenation of benzyl or p-methoxybenzyl or equivalent esters optionally in the presence of a base such as $Li_2CO_3$, $Na_2CO_3$, $K_2CO_3$. $NaHCO_3$ or the like and in the presence of a transition metal catalyst such as 10% palladium on charcoal, palladium on barium sulphate or the like. Such methods also include mild base hydrolysis, for example hydrolysis of the methyl ester by the controlled addition of LiOH, NaOH or the like added at a rate to maintain the pH of the solution in the region 7.5–9. The methoxymethyl ester may also be employed.

The present invention also provides a process for the preparation of a compound of the formula (XVIII):

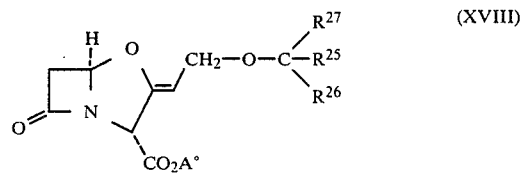

where $CO_2A°$ is an ester group and $R^{27}$ is a hydrogen atom or an alkyl group of 1–4 carbon atoms, $R^{25}$ is a hydrogen atom or an alkyl group of 1–4 carbon atoms and $R^{26}$ is a group such that the $CR^{27}R^{25}R^{26}$ moiety is an inert organic group of up to 18 carbon atoms; which process comprises the reaction of a corresponding ester of clavulanic acid with a compound of the formula (XIX):

wherein X is I, Br, or Cl and $R^{27}$, $R^{25}$ and $R^{26}$ are as defined in relation to formula (XVIII); in the presence of silver ions.

Most suitably the silver ions are provided by silver oxide. Generally about 1–2 equivalents are employed per equivalent of the ester of clavulanic acid.

Most suitably the reaction is carried out in the presence of calcium oxide. Generally about 1–2 equivalents of powdered calcium oxide are employed per equivalent of clavulanic acid ester used.

The compounds of the formula (XVIII) are naturally part of this invention as are the corresponding free acid and its salts which may be prepared by hydrolysis or hydrogenolysis of an appropriate ester as hereinbefore described.

Suitably $R^{27}$ is hydrogen, methyl, ethyl, n-propyl or n-butyl.

Suitably $R^{25}$ is hydrogen, methyl, ethyl, n-propyl or n-butyl.

Most suitably $R^{27}$ is hydrogen and most suitably $R^{25}$ is hydrogen. Thus certain particularly suitable $CR^{27}R^{25}R^{26}$ moieties are of the formula $CH_2R^{18}$ where $R^{18}$ is as defined in relation to formula (VIII).

Most suitably $CR^{27}R^{25}R^{26}$ is a group of the formula $CH_2R^{27}$ where $R^{27}$ is as defined in relation to formula (XVI).

Favoured values for $R^{26}$ include the hydrogen atom and the methyl, ethyl, n-propyl, n-butyl, n-pentyl, iso-propyl, vinyl, benzyl, p-methoxybenzyl and the like.

Particularly suitable values for $R^{26}$ include the hydrogen atom and the methyl, ethyl, benzyl and vinyl groups.

Particularly favoured values for $R^{26}$ are the hydrogen atom and the methyl and ethyl groups.

A preferred value for $R^{26}$ is the hydrogen atom. A further preferred value for $R^{26}$ is the methyl group.

The reaction of the ester of clavulanic acid with the compound of the formula (XIX) is generally carried out in an inert medium at a non-extreme temperature.

Suitable solvents for the reaction include hydrocarbon solvents such as benzene, toluene and the like and other conventional solvents such as ethyl acetate, tetrahydrofuran, acetone and the like.

The reaction may be best effected at a temperature of from about 10° to about 100° C., for example 30°-80° C.

It is desirable that the reaction mixture is maintained under anhydrous conditions.

Once the reaction is over (for example as judged by tlc) the mixture is allowed to cool, filtered to remove suspended solids and then evaporated. If desired the resulting material can be purified by such conventional procedures as column chromatography.

The salts of the compounds of the formula (IIa) are most suitably provided in crystalline form. This is most conveniently effected by crystallising the amorphous salt from a suitable solvent. Suitable solvents include aqueous acetonitrile, aqueous acetone, aqueous tetrahydrofuran and the like. In such mixed aqueous solvents systems it is most suitable that water is present by only a small percentage, for example 1-5% v/v. Other solvents include ethyl acetate, acetone diethyl ether mixtures and the like.

In general the lithium salt may be crystallised from the solvents which contain a few percent of water whereas other salts, for example the sodium salt, generally are more easily obtained from the solvents free of added water.

The salt of the compounds of the formula (IIa) most readily obtained in crystalline form is the lithium salt.

Crystalline salts of this invention have acceptable stability if stored under cool, dry conditions. The lithium salts are usually favoured salts for storage.

Other crystalline salts which are envisaged are the crystalline sodium, potassium and calcium salts.

As is well known in the art, crystalline salts are most readily prepared from the non-crystalline salts when of a good level of purity. Thus it may be convenient to prepare certain crystalline salts by first forming a lithium salt of good purity and converting this to an alternative salt also of good purity which may then be encouraged to crystallise.

[The preparation of diazo compounds is described in Houben-Weyl, Methoden der Organischen Chemie, Vol 10/4, 4th Edition.]

EXAMPLE 1

Preparation of Methyl 9-O-methylclavulanate

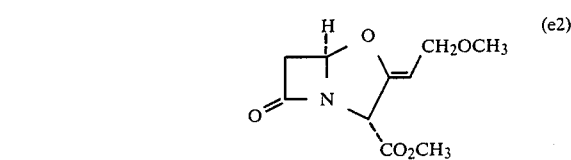

Benzyl clavulanate (e1) (1.5 g) in methanol (10 ml) was hydrogenated over 10% palladium on charcoal (0.4 g) for ½ hour at ambient temperature and pressure. The solution was filtered through celite and treated with a solution of diazomethane in ether at 0° C. The solution was left at 0° C. overnight, the solvent evaporated and the oil chromatographed on silica gel to yield as the second eluted product crude (e2) (35 mg). Rechromatography provided the title product as a colourless oil (15 mg).

I.r. (CHCl$_3$): 1800, 1750, 1695 cm$^{-1}$;

N.m.r. (CDCl$_3$): 3.03 (1H, dd, J 17 Hz, J' 1 Hz, 6β-C$\underline{H}$), 3.53 (1H, dd, J 17 Hz, J' 2.5 Hz, 6α-C$\underline{H}$), 3.31 (3H, s, OC$\underline{H}_3$), 3.79 (3H, s, CO$_2$C$\underline{H}_3$), 4.03 (2H, d, J 7 Hz, C$\underline{H}_2$OCH$_3$), 4.88 (1H, brt, J 7 Hz, olefinic C$\underline{H}$), 5.08 (1$\underline{H}$, m, 3-C$\underline{H}$), 5.70δ (1H, dd, J 2.5 Hz, J' 2.5 Hz, 5-C$\underline{H}$).

The approximate β-lactamase inhibition I$_{50}$ values in μg/ml for (e2) were as follows:

| | |
|---|---|
| Escherichia coli JT4 | 0.9 |
| Klebsiella aerogenes E70 | 0.25 |
| Staphylococcus aureus Russell | 0.5 |
| Escherichia coli JT410 | 3.1 |
| P. moig, Cr. | 0.68 |
| Pseudomonas aeruginosa | 1.9 |
| Citrobacter mantio | 0.45 |

EXAMPLE 2

Preparation of Benzyl 9-O-methylclavulanate

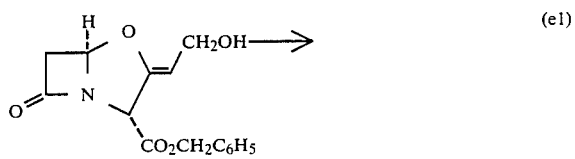

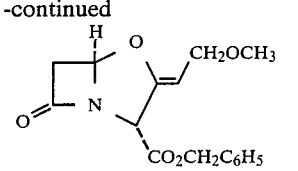

Benzyl clavulanate (e1) (300 mg) was dissolved in dry methylene dichloride (25 ml) and cooled to 0° C. Boron trifluoride etherate (5 drops) was added at 0° C. followed by a solution of diazomethane in ether. The reaction was stirred at 0° C. for one hour and washed with 3% sodium bicarbonate solution (2×25 ml). The organic phase was dried over magnesium sulphate and evaporated; chromatographic purification gave the title compound (e3) (66 mg).

I.r. (CHCl$_3$): 1800, 1745, 1695 cm$^{-1}$;

N.m.r. (CDCl$_3$): 3.10 (1H, d, J 17 Hz, 6β-CH), 3.35 (3H, s, OCH$_3$), 3.60 (1H, dd, J 17 Hz, J' 2.5 Hz, 6α-CH), 4.12 (2H, d, J 8 Hz, CH$_2$OCH$_3$), 4.94 (1H, t, J 8 Hz, =CH—CH$_2$), 5.24 (1H, br.s, 3-CH), 5.32 (2H, s, CO$_2$CH$_2$Ph), 5.82 (1H, d, J 2.5 Hz, 5-CH), 7.51δ (5H, s, CO$_2$CH$_2$Ph).

The approximate β-lactamase inhibition I$_{50}$ values in μg/ml for (e3) were as follows:

| | |
|---|---|
| Escherichia coli JT4 | 0.1 |
| Klebsiella aerogenes E70 | 0.05 |
| Staphylococcus aureus Russell | 0.05 |
| Proteus mirabilis C889 | <0.07 |
| Pseudomonas aeruginosa | 1.4 |
| Pseudomonas dalgleish | <0.07 |
| Citrobacter mantio | 1.1 |

EXAMPLE 3

Preparation of Sodium 9-O-methylclavulanate

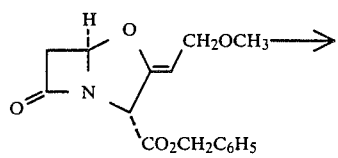

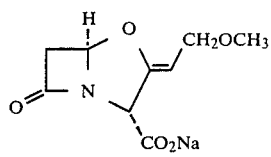

The ether (e3) (30 mg) was dissolved in tetrahydrofuran (3 ml) and 10% palladium on charcoal (10 mg) added. The solution was hydrogenated at ambient temperature and pressure for 15 minutes, filtered and sodium bicarbonate (8.4 mg) in 0.5 ml water was added. The solvent was evaporated to yield the sodium salt (e4) as an amorphous solid after trituration with ether (15 mg).

I.r. (KBr disc): 1790, 1690, 1615 cm$^{-1}$;

N.m.r. (D$_2$O): 3.07 (1H, d, J 17 Hz, 6β-CH), 3.27 (3H, s, OCH$_3$), 3.54 (1H, dd, J 17 Hz, J' 2.5 Hz, 6α-CH), 4.04 (2H, d, J 8 Hz, CH$_2$OCH$_3$), 4.87 (1H, t, J 8 Hz, =CH—CH$_2$), 4.93 (1H, s, 3-CH), 5.69δ (1H, d, J 2.5 Hz, 5-CH).

The approximate β-lactamase inhibition I$_{50}$ values in μg/ml for (e4) were as follows:

| | |
|---|---|
| Escherichia coli JT4 | 0.18 |
| Klebsiella aerogenes E70 | 0.07 |
| Staphylococcus aureus Russell | 0.05 |
| Proteus mirabilis C889 | 0.01 |

EXAMPLE 4

Preparation of Methyl 9-O-benzylclavulanate

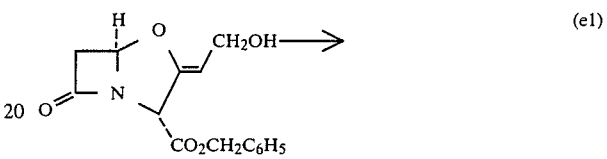

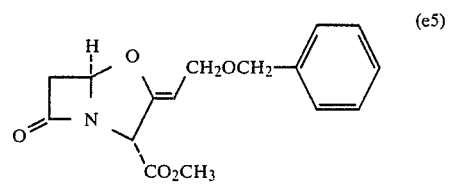

Benzyl clavulanate (e1) (300 mg) in methylene chloride (25 ml) was cooled to −30° C. and treated with boron trifluoride etherate (5 drops) followed by a solution of diazotoluene in ether. The solution was stirred at −30° C. for one hour and washed with 3% sodium bicarbonate solution (3×25 ml). The organic phase was dried over magnesium sulphate and evaporated to yield after chromatography crude benzyl 9-O-benzylclavulanate (150 mg) as an oil. The oil was dissolved in tetrahydrofuran (5 ml) and hydrogenated at ambient temperature and pressure over 10% Pd/C (20 mg) for 20 minutes. The solution was filtered and treated with a solution of diazomethane in ether at 0° C. Evaporation of the solvent and chromatography provided the title product (e 5) (30 mg) as a colourless oil.

I.r. (CHCl$_3$): 1800, 1750, 1695 cm$^{-1}$;

N.m.r. (CDCl$_3$): 3.12 (1H, d, J 17 Hz, 6β-CH), 3.62 (1H, dd, J 17 Hz, J' 2.5 Hz, 6α-CH), 3.89 (3H, s, CO$_2$CH$_3$), 4.25 (2H, d, J 8 Hz, =CH—CH$_2$O), 4.61 (2H, s, OCH$_2$Ph), 5.02 (1H, br.t., J 8 Hz, =CH—CH$_2$), 5.18 (1H, m, 3-CH), 5.82 (1H, d, J 2.5 Hz, 5-CH), 7.49δ(5H, s, OCH$_2$Ph); [α]$_D^{20}$ = +15° (c=1.37; MeOH).

| Antibacterial Activity in Vitro (μg/ml) | |
|---|---|
| Staphylococcus aureus Oxford | 15–31 |
| Staphylococcus aureus Russell | 8–15 |
| Klebsiella aerogenes A. | >500 |
| β-Lactamase Inhibition I$_{50}$ (μg/ml) | |
| Escherichia coli JT4 | 0.8 |
| Klebsiella aerogenes E70 | 0.8 |
| Staphylococcus aureus Russell | 0.005 |

EXAMPLE 5

Preparation of Sodium 9-O-benzylclavulanate

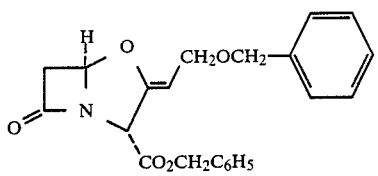
(e1)

Crude benzyl 9-O-benzylclavulanate (150 mg) was dissolved in tetrahydrofuran (5 ml) and hydrogenated at ambient temperature and pressure over 10% Pd/C (20 mg) for 20 minutes. The solution was filtered and treated with sodium bicarbonate (15 mg) in 1 ml water. The solvent was evaporated and the residue taken up in water (10 ml) and washed with ethyl acetate (3 × 10 ml). The aqueous phase was evaporated to yield the required sodium salt as an amorphous solid after trituration with ether (e6) (35 mg).

I.r. (KBr): 1790, 1690, 1615 cm$^{-1}$;

N.m.r. (D$_2$O): 3.09 (1H, d, J 17 Hz, 6β-CH), 3.59 (1H, dd, J 17 Hz, J' 2.5 Hz, 6α-CH), 4.20 (2H, d, J 8 Hz, =CH—CH$_2$O), 4.48 (2H, s, OCH$_2$Ph), 4.97 (1H, br.t., J 8 Hz, =CH—CH$_2$O), 4.99 (1H, m, 3-CH), 5.74 (1H, d, J 2.5 Hz, 5-CH), 7.42δ (5H, s, OCH$_2$Ph); $[\alpha]_D^{20} = +22.5°$ (c=1.15; 50% aqueous MeOH).

| Antibacterial Activity in Vitro (μg/ml) | |
|---|---|
| *Klebsiella aerogenes* A. | 125 |
| *Staphylococcus aureus* Oxford | 4.0 |
| *Staphylococcus aureus* Russell | 8.0 |
| β-Lactamase Inhibition I$_{50}$ (μg/ml) | |
| *Escherichia coli* JT4 | 0.1 |
| *Klebsiella aerogenes* E70 | 0.04 |
| *Staphylococcus aureus* Russell | 0.005 |
| *Proteus mirabilis* C889 | 0.02 |
| *Pseudomonas dalgleish* | 0.008 |

EXAMPLE 6

Preparation of Benzyl 9-O-ethoxycarbonylmethylclavulanate

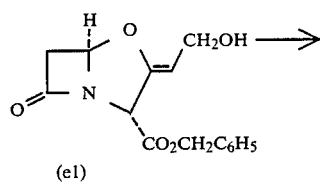
(e1)

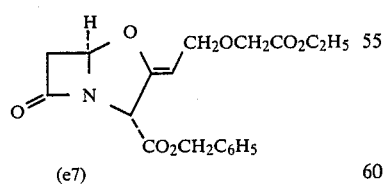
(e7)

Benzyl clavulanate (e1) (1.44 g) was dissolved in dry methylene dichloride (100 ml) and boron trifluoride etherate (25 drops; 0.3 ml) was added at −30° C. Ethyl diazoacetate (2.90 g; 5 equivalents) in methylene dichloride (10 ml) was added dropwise over half an hour and the mixture stirred at −30° C. to −10° C. for one hour. The solution was washed with 3% sodium bicarbonate solution (3 × 50 ml) and dried over magnesium sulphate. The solvent was evaporated at room temperature and the residue chromatographed to yield the title compound (e7) as a colourless oil (600 mg).

I.r. (CHCl$_3$): 1800, 1745, 1695 cm$^{-1}$;

N.m.r. (CDCl$_3$): 1.29 (3H, t, J 8 Hz, —CO$_2$CH$_2$CH$_3$), 3.00 (1H, d, J 17 Hz, 6β-CH), 3.50 (1H, dd, J 17 Hz, J' 2.5 Hz, 6α-CH), 3.97 (2H, s, CH$_2$CO$_2$Et), 3.90 to 4.50 (4H, complex pattern, =CH—CH$_2$ and CO$_2$CH$_2$CH$_3$), 4.79 (1H, t, J 8 Hz, =CH—CH$_2$), 5.14 (1H, brs, 3-CH), 5.23 (2H, s, CO$_2$CH$_2$Ph), 5.72 (1H, d, 2.5 Hz, 5-CH), 7.37δ (5H, s, CO$_2$CH$_2$Ph). $[\alpha]_D^{21} = +35.3°$ (c=1.29; MeOH).

The approximate β-lactamase inhibition I$_{50}$ values in μg/ml for (e7) were as follows:

| | |
|---|---|
| *Escherichia coli* JT4 | 0.14 |
| *Klebsiella aerogenes* E70 | 0.30 |
| *Staphylococcus aureus* Russell | 0.12 |
| *Proteus mirabilis* C889 | 1.0 |
| Antibacterial Activity in Vitro (μg/ml) | |
| *Klebsiella aerogenes* A. | >500 |
| *Staphylococcus aureus* Oxford | 125 |
| *Staphylococcus aureus* Russell | 125 |

EXAMPLE 7

Preparation of Sodium 9-O-ethoxycarbonylmethylclavulanate

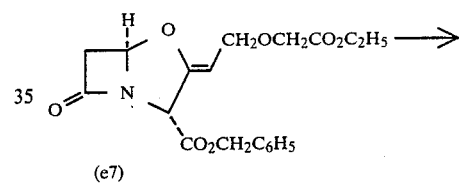
(e7)

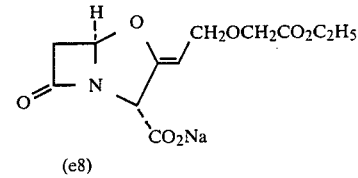
(e8)

The ester (e7) (188 mg) was dissolved in dry tetrahydrofuran (5 ml) and 10% Pd/C (65 mg) was added. The solution was hydrogenated at ambient temperature and pressure for fifteen minutes, the solution filtered through kieselguhr and sodium bicarbonate (42 mg) in water (1 ml) was added. The solvent was evaporated and the residue chromatographed on silica gel eluting with butanol/ethanol/water, 4/1/1. Trituration of the product with ether gave the sodium salt (e8) as an amorphous solid (95 mg).

I.r.(KBr): 1790, 1740, 1690, 1600 cm$^{-1}$;

N.m.r. (D$_2$O): 1.27 (3H, t, J 8 Hz, CO$_2$CH$_2$CH$_3$), 3.09 (1H, d, J 17 Hz, 6β-CH), 3.57 (1H, dd, J 17 Hz, J' 2.5 Hz, 6α-CH), 4.14 (2H, s, OCH$_2$CO$_2$Et), 4.21 (4H, doublet and quartet superimposed, J=J' 8 Hz, =CH—CH$_2$— and CO$_2$CH$_2$CH$_3$), 4.86 (1H, t, J 8 Hz, =CH—CH$_2$—), 4.96 (1H, brs, 3-CH), 4.71δ (1H, d, J 2.5 Hz, 5-CH). $[\alpha]_D^{21} = 36.5°$ (c=1.15; 50% aqueous MeOH).

The approximate β-lactamase inhibition I$_{50}$ values in μg/ml for (e8) were as follows:

| | |
|---|---|
| *Escherichia coli* JT4 | 0.16 |
| *Klebsiella aerogenes* E70 | 0.034 |
| *Staphylococcus aureus* Russell | 0.044 |
| *Proteus mirabilis* C889 | 0.025 |
| Antibacterial Activity in Vitro (μg/ml) | |
| *Escherichia coli* 10418 | 31.0 |
| *Klebsiella aerogenes* A. | 15.0 |
| *Proteus mirabilis* C977 | 62.0 |
| *Staphylococcus aureus* Oxford | 15.0 |
| *Staphylococcus aureus* Russell | 15.0 |

EXAMPLE 8

Preparation of Sodium 9-O-ethoxycarbonylmethylclavulanate

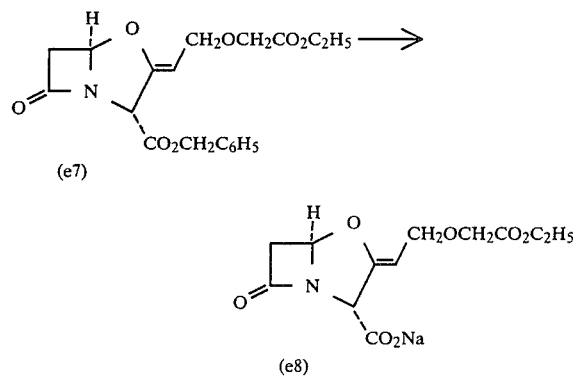

The ester (e7) (112 mg) was hydrolysed using N NaOH at constant pH (using a pH stat) until hydrolysis was complete. Chromatography yielded the sodium salt as an amorphous solid after trituration with ether (e8) (15 mg).

EXAMPLE 9

Preparation of Benzyl 9-O-benzyloxycarbonylmethylclavulanate

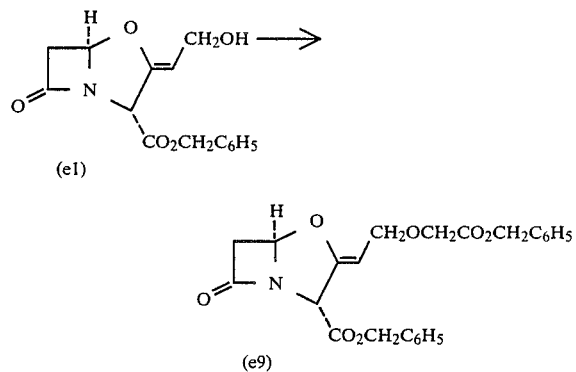

Benzyl clavulanate (e1) (1.8 g) was dissolved in dry methylene chloride (100 ml) and boron trifluoride etherate (25 drops; 0.3 ml) was added at −30° C. Benzyl diazoacetate (5 g of 66% pure material) in methylene chloride (20 ml) at −30° C. was added dropwise over half an hour and the mixture stirred at −30° C. to −10° C. for one hour. The solution was washed with 3% sodium bicarbonate solution (2×50 ml) and dried over magnesium sulphate. The solvent was evaporated at room temperature and the residue chromatographed over silica gel eluting with cyclohexane/ethyl acetate.

The resulting somewhat impure oil was rechromatographed to yield pure title material (e9) as a colourless oil (0.32 g).

I.r.(film): 1800, 1760, 1750, 1695 cm$^{-1}$;

N.m.r. (CDCl$_3$): 7.29 (10H, aromatic H), 5.58 (1H, d, J 2.5Hz, 5-C$\underline{H}$), 5.13 (4H, C$\underline{H_2}$Ph), 5.03 (1H, 3-C$\underline{H}$), 4.79 (1H, t, J $\overline{7}$Hz, =C$\underline{H}$—C$\overline{H_2}$), 4.16 (2H, d, $\overline{J}$ 8 Hz, =CH—C$\underline{H_2}$—), 4.00 (2H, s, =CH—CH$_2$—O—C$\underline{H_2}$—), 3.40–2.95δ (2H, dd, J 18 Hz, 6-C$\underline{H_2}$).

The benzyl diazoacetate was prepared by the reaction of benzylchloroformate and diazomethane at 4° C. for 3 days which yielded a 66% pure product as an oil.

EXAMPLE 10

Preparation of Di-sodium 9-O-carboxymethylclavulanate

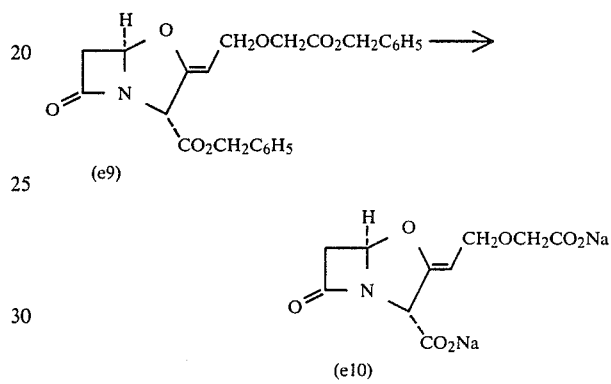

The ester (e9) (260 mg) was dissolved in a mixture of tetrahydrofuran and water (5:1, 12 ml) and sodium bicarbonate (100 mg) and 10% Pd/C (150 mg) were added. The solution was hydrogenated at ambient temperature and pressure for 30 minutes, filtered and evaporated to yield the desired disodium salt (e10).

I.r. (KBr): 1780, 1685, 1600, 1425 cm$^{-1}$.

EXAMPLE 11

Preparation of Benzyl 9-O-cyanomethylclavulanate

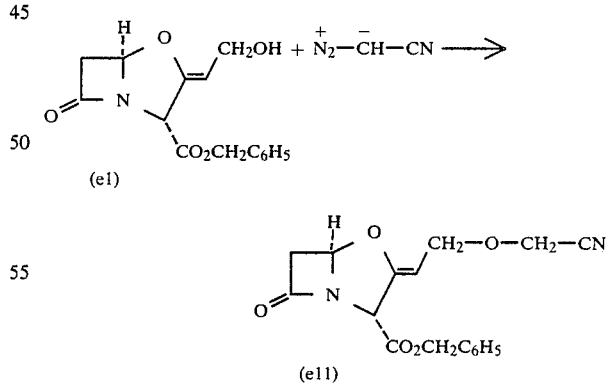

A solution of benzyl clavulanate (e1) (5.18 g) in methylene dichloride (50 ml) was dried over 4 A molecular sieves and filtered. The solution was cooled to −40°–−30° C. and 1 ml boron trifluoride etherate was added. A solution of diazoacetonitrile (prepared from aminoacetonitrile hydrochloride (9.3 g) as in Houben-Weyl vol 10/4) in methylene chloride (250 ml) was added dropwise over 1 hour maintaining the temperature at −40°—−30° C. The mixture was then allowed to warm to −10° C. After 1 hour at −10° C. the solution was washed with 3 portions of dilute sodium bicarbonate solution (200 ml), dried over calcium chloride and evaporated to give a brown gum. The product was purified by column chromatography (Kieselgel; cyclohexane:ethyl acetate 3:1 followed by 1:1) to give a slightly impure product. Repeat of the chromatography (same system) gave the desired product (e11) (1.56 g).

I.r. (film): 1805, 1750, 1698 cm$^{-1}$.

N.m.r. (CDCl$_3$): δ3.02 (1H, doublet, J 17 Hz), 3.45 (1H, double doublet, J 17 Hz and 3 Hz), 4.01 (2H, singlet), 4.14 (2H, doublet, J 7 Hz), 4.70 (1H, triplet with fine coupling, Jtrip 7 Hz), 5.06 (1H, singlet) 5.14 (2H, singlet), 5.66 (1H, singlet with fine coupling), 3.28 (5H, singlet).

EXAMPLE 12

Preparation of Sodium 9-O-cyanomethylclavulanate

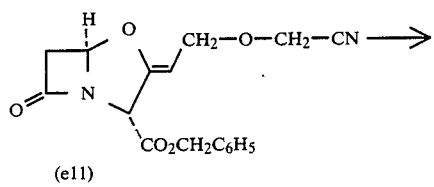

(e11)

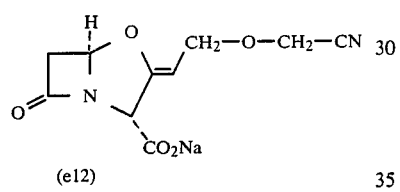

(e12)

A mixture of benzyl 9-(O-cyanomethyl)clavulanate (e11) (1.56 g) and sodium bicarbonate (0.399 g) in tetrahydrofuran/water (30 ml 5:1 tetrahydrofuran:water) was hydrogenated over 10% palladium charcoal (0.5 g) at room temperature and atmospheric pressure, until the requisite amount of hydrogen had been absorbed. The mixture was then filtered and the catalyst washed with water. The combined filtrates were then evaporated until most of the tetrahydrofuran had been removed. The remaining aqueous solution was washed with ethyl acetate and freeze-dried to yield the desired product (e12) (913 mg) as a brown solid. A sample (535 mg) was passed through a short column of Kieselgel using n-butanol:H$_2$O:EtOH (4:1:1) solvent to yield (e12) (213 mg) as a pale yellow solid.

N.m.r. (D$_2$O): δ3.24 (1H, doublet J 16 Hz), 3.66 (1H, double doublet, J 16 Hz and 3 Hz), 4.30 (2H, doublet, J 7Hz), 4.40 (2H, singlet), 4.91 (1H, triplet with fine coupling, J 7 Hz), 5.00 (1H, singlet), 5.78 (1H, doublet, 3Hz).

I.r. (KBr disc): 1780, 1610 (broad) cm$^{-1}$.

EXAMPLE 13

Preparation of Benzyl 9-O-(p-nitrobenzyl)clavulanate

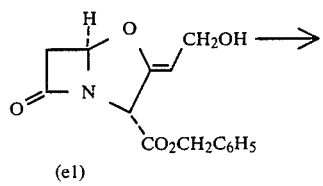

(e1)

-continued

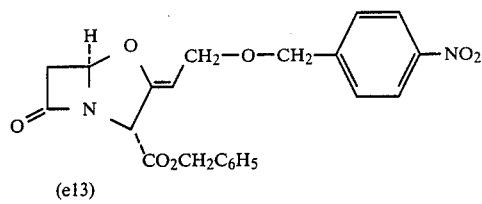

(e13)

A solution of benzyl clavulanate (e1) (4.33 g) in methylene chloride (50 ml) was dried over 4 A molecular sieves for ½ hour. The solution was then filtered and cooled to −30° C. Boron trifluoride etherate (0.8 ml) was then added. A solution of 4-nitrophenyl diazomethane (7.34 g) in methylene chloride (150 ml) was then added to the stirred solution at −30° C., over 1 hour. The mixture was then warmed to −10° C. over a period of 1 hour. The solution was then washed with sodium bicarbonate solution (3×150 ml), dried over magnesium sulphate and evaporated. Repeated chromatography (twice with cyclohexane:ethyl acetate 1:1, and once with methylene chloride as eluant) on Kieselgel H gave the pure ether (e13) (230 mg).

I.r. (film): 1800, 1750, 1700, 1520 cm$^{-1}$.

N.m.r. (CDCl$_3$): 2.98 (1H, doublet, J 17 Hz), 3.44 (1H, double doublet, J 17 Hz and 3 Hz), 4.09 (2H, doublet, J 7 Hz), 3.45 (2H, singlet), 4.8 (1H, triplet with fine coupling, J 7 Hz), 5.05 (1H, singlet), 5.14 (2H, singlet), 5.63 (1H, doublet with fine coupling), 7.27 (5H, singlet), 7.38 (2H, doublet, J 9 Hz), 8.11 (2H, doublet, J 9 Hz).

EXAMPLE 14

Preparation of Benzyl 9-O-allylclavulanate

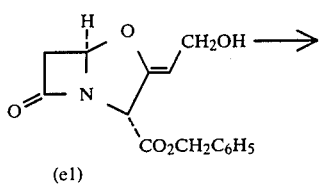

(e1)

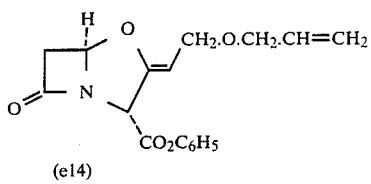

(e14)

(i) N-Nitroso-N-allylbenzamide

A solution of nitrogen dioxide (24.1 g) in carbon tetrachloride (150 ml) was added to a stirred mixture of anhydrous sodium acetate (45 g) and carbon tetrachloride (150 ml) at −20° C. N-allylbenzamide (28.4 g) in carbon tetrachloride (150 ml) was added to the stirred mixture at −5° C. which was then stirred at 0° C. for 0.5 hour. This was washed with aqueous sodium bicarbonate (2×400 ml), dried, and evaporated to give N-nitroso-N-allylbenzamide (28.5 g).

ν$_{max}$ (liquid film): 1710, 1650, 1600, 1570, 1355, 1285, 1155, 1040 and 920 cm$^{-1}$, δ(CDCl$_3$): 7.83–7.20 (5H, m, ArH̲), 6.03–4.83 (3H, m,

and 4.33 (2H, broad d, J 4 Hz).

(ii) 3-Diazoprop-1-ene

Pyrrolidine (4.53 ml) was added to a solution of N-nitroso-N-allylbenzamide (9.5 g) in methylene chloride (100 ml) at −20° C. and the mixture was stirred at −20° C. for 15 minutes to give a solution of 3-diazoprop-1-ene.

$v_{max}$ (CH$_2$Cl$_2$): 2030 cm$^{-1}$. This solution was then stored at 0° C. until use.

(iii) Benzyl 9-O-allylclavulanate

Boron trifluoride etherate (1 ml) was added to a solution of benzyl clavulanate (2.89 g) in methylene chloride (150 ml) at −30° C. The solution of 3-diazoprop-1-ene prepared above was added to the mixture at −30° C. and the solution was stirred at −30° C. to −10° C. for hour. This was washed with aqueous sodium bicarbonate (2×200 ml), dried and evaporated to give the crude product as an oil which was chromatographed over silica gel (50 g). Elution of the column with cyclohexaneethyl acetate gave benzyl 9-(O-allyl)-clavulante (e14) (0.92 g) as a colourless liquid, [α]$_D$+45.3° (CHCl$_3$; c, 1.0), $v_{max}$ (liquid film): 1800, 1750, 1695, 1300, 1175, 1030, 1010, 995 cm$^{-1}$.

δ(CDCl$_3$): 7.37 (5H, s, Ar—H), 6.05–5.70

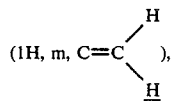

5.60 (1H, d, J 2.5 Hz, 5-CH), 5.30–5.10

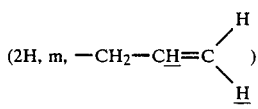

5.13 (2H, s, —CH$_2$Ph), 5.03 (1H, m, 3-CH), 4.79 (1H, broad t, J 8 Hz, 8-CH), 4.01 (2H, d, J 8 Hz, 9-CH), 3.86 (2H, broad d, J 7 Hz, —CH$_2$—CH=CH$_2$), 3.41 (1H, dd, J 18 Hz, J' 2.5 Hz, 6α-CH), 2.98 (1H, d, J 18 Hz, 6β-CH).
(Found: C, 65.85; H, 5.65; N, 4.45%. C$_{18}$H$_{19}$NO$_5$ requires C, 65.65; H, 5.8; N, 4.25%).

EXAMPLE 15

Preparation of Benzyl 9-O-(2'-benzyloxycarbonylethyl)clavulanate

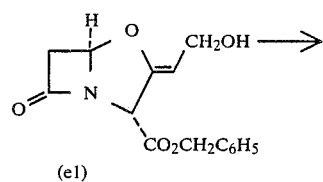

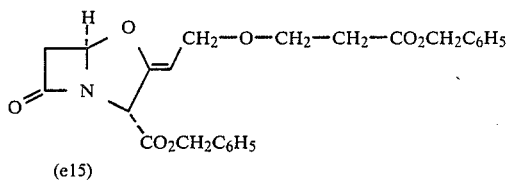

(i) Benzyl N-nitroso-N-benzyloxycarbonyl-β-alanate

A solution of nitrogen dioxide (6.9 g) in carbon tetrachloride (40 ml) was added to a stirred solution of anhydrous sodium acetate (12.3 g) and carbon tetrachloride (40 ml) at −20° C. Benzyl N-benzyloxycarbonyl-β-alanate (12.95 g) in carbon tetrachloride (50 ml) was added to the stirred mixture at −5° C. which was then stirred at 0° C. for 0.5 hour. The reaction mixture was washed with aqueous sodium bicarbonate (2×100 ml) and the carbon tetrachloride solution was dried and evaporated to give benzyl N-nitroso-N-benzyloxycarbonyl-β-alanate (12.5 g) as an oil, $v_{max}$ (CCl$_4$): 1745, 1705, 1520, 1400, 1350, 1175, 1140, 1095, 960 cm$^{-1}$, δ(CDCl$_3$): 7.30 (10H, s, ArH), 5.46 (2H, s, CH$_2$Ph), 4.90 (2H, s, CH$_2$Ph), 3.92 (2H, t, J 7 Hz), and 2.36 (2H, t, J 7 Hz), (The n.m.r. spectrum indicated that the starting material and this oil were only about 73% pure).

(ii) Benzyl 9-O-(2'-benzyloxycarbonylethyl)clavulanate

Pyrrolidine (0.58 ml) was added to a solution of benzyl N-nitroso-N-benzyloxycarbonyl-β-alanate (3.24 g) in methylene chloride (25 ml) at −20° C. and the mixture was stirred at −20° C. for 15 minutes to give a solution of benzyl 3-diazopropionate which was kept at 0° C. for the next stage.

Boron trifluoride etherate (0.5 ml) was added to a solution of benzyl clavulanate (1 g) in methylene chloride (150 ml) at −30° C. The solution of benzyl 3-diazopropionate prepared above was added to the mixture at −30° C. and the solution was stirred at −30° C. to −10° C. for 1 hour. This was washed with aqueous sodium bicarbonate (2×50 ml), dried and evaporated to give the crude product as an oil which was chromatographed over silica gel (30 g). Elution of the column with cyclohexane-ethyl acetate gave benzyl 9-[O-(2-benzyloxycarbonylethyl)] clavulanate (e15) (0.21 g) as a colourless liquid, [α]$_D$ 29.3° (CHCl$_3$; c, 1.0), $v_{max}$ (liquid film): 1805, 1740, 1700, 1240, 1170, 1100, 1040 and 1020 cm$^{-1}$, δ(CDCl$_3$): 7.28 (10H, s, Ar—H), 5.60 (1H, d, J 2.5 Hz, 5-CH), 5.14 (2H, s, CH$_2$Ph), 5.09 (2H, s, CH$_2$Ph), 5.02 (1H, m, 3-CH), 4.74 (1H, broad t, J 8 Hz, 8-CH), 4.01 (2H, broad d, J 8 Hz, 9-CH), 3.60 (2H, t, J 7 Hz), 3.41 (1H, dd, J 18 Hz, J' 2.5 Hz, 6α-CH), 2.99 (1H, d, J 18 Hz, 6β-CH) and 2.57 (2H, t, J 7 Hz). M$^+$ 451.1626, C$_{25}$H$_{25}$NO$_7$ requires M$^+$ 451.1631.

EXAMPLE 16

Preparation of Disodium 9-O-(2'-carboxyethyl)clavulanate

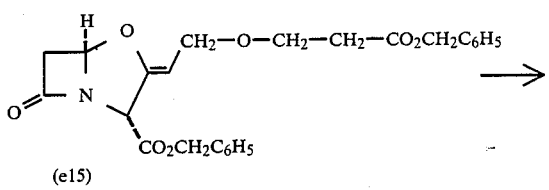
(e15)

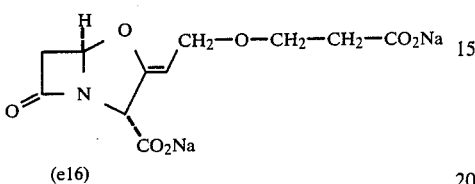
(e16)

A mixture of benzyl 9-[O-(2-benzyloxycarbonylethyl)]clavulanate (e15) (0.17 g) and sodium bicarbonate (0.063 g) in tetrahydrofuran/water 5:1, 12 ml) was hydrogenated in the presence of 10% palladium charcoal (0.1 g) at room temperature and pressure for 0.5 hour. The mixture was filtered and the filtrate evaporated to give disodium 9-O-(2'-carboxyethyl)clavulanate (e16) (0.084 g).

$\nu_{max}$(KBr): 1780, 1690, 1620, 1390, 1310, 1195, 1155, 1085, 1040 and 895 cm$^{-1}$.

$\delta$(D$_2$O): 5.65 (1H, d, J 2.5 Hz, 5-CH), 4.87 (1H, s, 3-CH), 4.81 (1H, broad t, J 8 Hz, 8-CH), 4.06 (2H, d, J 8 Hz, 9-CH$_2$), 3.63 (3H, t, J 7 Hz), 3.51 (1H, dd, J 18 Hz, J' 2.5 Hz, 6α-CH), 3.05 (1H, d, J 18 Hz, 6β-CH), and 2.49 (3H, t, J 7 Hz).

EXAMPLE 17

Preparation of Benzyl 9-O-acetonyl clavulanate

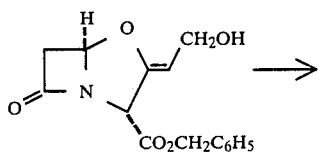
(e1)

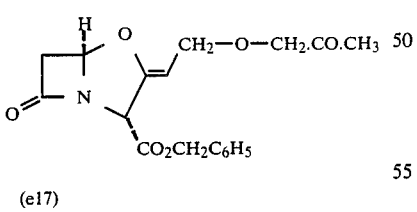
(e17)

To a solution of benzyl clavulanate (e1) (1.0 g) and diazoacetone (1.4 g) in methylene chloride (30 ml) was added boron trifluoride diethyletherate (20 drops), and the solution stirred at −10° C. for 2.0 hours. The reaction mixture was quenched with dilute bicarbonate solution. The organic extract was washed with sodium chloride solution, dried over magnesium sulphate and evaporated. Silica gel chromatography (eluting with ethyl acetate/cyclohexane) yielded the title product (e17) (190 mg) as a colourless oil.

I.r. (CHCl$_3$): 1800, 1730–1760, 1695 cm$^{-1}$;

N.m.r. (CDCl$_3$): 2.10 (3H, s, —CH$_3$), 2.96 (1H, d, J 17 Hz, 6β-CH), 3.36 (1H, dd, J 17 Hz, J' 2.5 Hz, 6α-CH), 3.99 (2H, d, J 7 Hz, =CH—CH$_2$), 4.68 (1H, t, J 7 Hz, =CH—CH$_2$), 5.03 (1H, brs, 3-CH), 5.20 (2H, s, —CH$_2$Ph), 5.70 (1H, d, J 2.5 Hz, 5-CH), 7.33 (5H, s, CO$_2$CH$_2$Ph). M (mass spectrometry) 345.

EXAMPLE 18

Preparation of Sodium 9-O-acetonylclavulanate

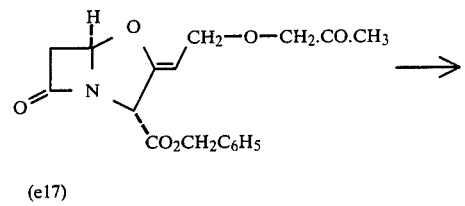
(e17)

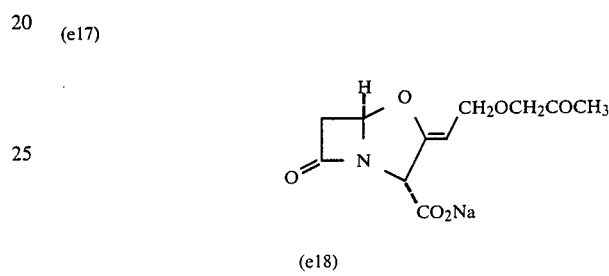
(e18)

The acetonyl ether benzyl ester (e17) (80 mg) was hydrogenated in a tetrahydrofuran/water mixture (5:1) in the presence of sodium bicarbonate (20 mg) and 10% palladium/charcoal (30 mg). After twenty minutes the catalyst was filtered off. The filtrate was diluted with water and extracted with ethyl acetate before freeze-drying. This yielded the title product as an off-white solid.

I.r. (KBr): 1780, 1720, 1690, 1610 cm$^{-1}$;

N.m.r. (CDCl$_3$): 2.09 (3H, s, —CH$_3$), 3.00 (1H, d, J 17 Hz, 6β-CH), 3.45 (1H, dd, J 17 Hz, J' 2.5 Hz, 6α-CH), 4.08 (2H, d, J 8 Hz, =CH—CH$_2$), 4.18

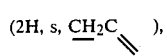
(2H, s, CH$_2$C$\diagdown^{\diagup\mathrm{O}}$), 4.80 (1H, t, J 8 Hz, =CH), 4.90 (1H, s, 3-CH), 5.65 (1H, d, J 2.5 Hz, 5-CH).

EXAMPLE 19

Preparation of Benzyl 9-O-(p-chlorophenacyl)clavulanate

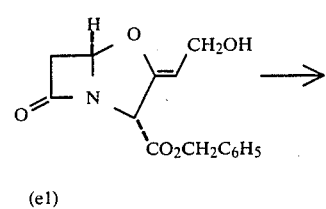
(e1)

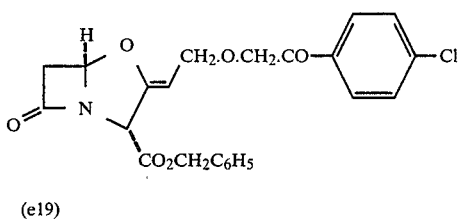

(e19)

Benzyl clavulanate (e1) (500 mg) was dissolved in methylene chloride (25 ml) and treated with α-diazo-p-chloroacetophenone (0.90 g). To the stirring solution at −20° C. was added boron trifluoride etherate (0.1 ml). The solution was stirred at −20° C. to −10° C. for 2.0 hours, washed with dilute sodium bicarbonate solution (×2), and the organic extract dried over magnesium sulphate. Evaporation of the solvent and silica gel chromatography (eluting with chloroform) yielded the title compound (e19) (130 mg).

I.r. (CHCl$_3$): 1805, 1750, 1695 cm$^{-1}$;

N.m.r. (CDCl$_3$): 3.10 (1H, d, J 17 Hz, 6β-C$\underline{H}$), 3.60 (1H, dd, J 17 Hz, J' 2.5 Hz, 6α-C$\underline{H}$), 4.36 (2H, s, J 7 Hz, =CH—C$\underline{H}_2$O—), 4.74

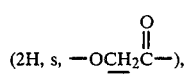

(2H, s, —OC$\underline{H}_2$C—), 5.00 (1H, t, J 7 Hz, =C$\underline{H}$—CH$_2$), 5.26 (1H, brs, 3-C$\underline{H}$), 5.37 (2H, s, CO$_2$C$\underline{H}_2$Ph), 5.82 (1H, d, J 2.5 Hz, 5-C$\underline{H}$), 7.48–8.12 (9H, m, Aryl).

EXAMPLE 20

Biological Activity a. When administered to mice the compounds of this invention do not exhibit a high level of toxicity, for example on sub-cutaneous administration the compounds of Examples 5 and 12 have LD$_{50}$ values of greater than 250 mg/kg.

b. When tested in standard MIC tests in combination with ampicillin the compounds of this invention are seen to enhance the effectiveness of the penicillin against various gram-positive and gram-negative organisms such as strains of *Staphylococcus aureus* Russell, *Klebsiella aerogenes, Proteus mirabilis* and *Escherichia coli*: for example the following MIC values against *Staphylococcus aureus* Russell were obtained for ampicillin in the presence of 1 μg/ml of certain compounds of the invention:

| Compound of Example No: | 3 | 5 | 9 | 10 | 11 | 14 | 15 | 16 |
|---|---|---|---|---|---|---|---|---|
| MIC (μg/ml): | 2 | 0.3 | 1.6 | 3 | 1.25 | 1.25 | 1 | 1 |

Ampicillin in the absence of synergist did not inhibit the growth of the test organism at a concentration of 250 μg/ml. None of the synergists inhibited the growth of the test organism at 5 μg/ml.

EXAMPLE 21

Preparation of Benzyl 9-O-[2'-(N-Benzyloxycarbonyl-N-methyl)aminoethyl]-clavulanate

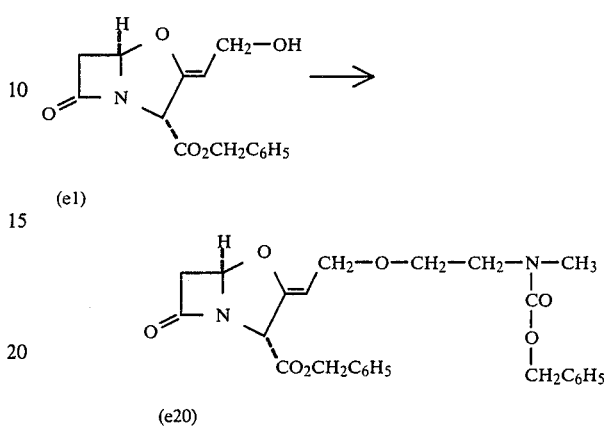

(i)

N-Methyl-N'-nitroso-N,N'-dibenzyloxycarbonyl-1,2-diaminoethane

To carbon tetrachloride (90 ml) stirred between −5° and 10° was added anhydrous sodium acetate (27.8 gm), followed by a solution of nitrogen dioxide (15.6 gm) in carbon tetrachloride (90 ml) at such a rate that the temperature did not rise above −5°. A solution of N-methyl-N,N'-dibenzyloxycarbonyl-1,2-diaminoethane (29 gm) in carbon tetrachloride (90 l) was then added to the stirred solution over 40 minutes maintaining the temperature at −10°. When the addition was complete the mixture was allowed to stir for 2 hours. The mixture was then washed with excess sodium bicarbonate solution, the aqueous phase was extracted with carbon tetrachloride and the combined organic phases were dried over magnesium sulphate and evaporated to yield 29.8 g of approximately 80% pure material.

(ii)

N-Methyl-N,N'-dibenzyloxycarbonyl-1,2-diaminoethane

To a stirred solution of N-Methyl-1,2-diaminoethane (7.4 gm) and triethylamine (20.2 gm) in chloroform (50 ml) at 0° was added dropwise over 30 minutes benzyl chloroformate (34.1 gm). The mixture was then left to warm to room temperature over one hour. The organic solution was then washed with water, citric acid solution, sodium bicarbonate solution and finally water again. The chloroform solution was dried over magnesium sulphate and evaporated to give a yellow oil (29.6 g).

(iii) Benzyl 9-O-[2'-(N-Benzyloxycarbonyl-N-Methyl)aminoethyl]-clavulanate

A stirred solution of N-methyl-N'-nitroso-N,N'-dibenzyloxycarbonyl-1,2-diaminoethane (3.71 gm) in methylene chloride (10 ml) was cooled to −30° and treated with pyrrolidine (0.71 gm). The mixture was allowed to stir at −25° to 30° for half an hour and then used as described below.

A solution of benzyl clavulanate (1.0 gm) in methylene chloride (10 ml) was cooled to −30° and treated with boron trifluoride etherate (0.5 ml). The solution of the diazo compound, prepared as described above, was then added to the stirred solution at such a rate as to keep the temperature below −25°. The mixture was then stirred for one hour gradually raising the temperature to −10°. Excess ice-cold sodium bicarbonate solution was then added and the organic phase separated. The aqueous phase was extracted with methylene chloride and the combined organic phases were washed with water, dried over magnesium sulphate and evaporated. Repeated chromatography of the residue gave the desired ether (e20).

I.R. (film), [No OH absorbtion], 1800, 1745 and 1700 cm−1. Thin layer chromatographic properties consistent with formula.

EXAMPLE 22

Preparation of Sodium 9-O-(p-nitrobenzyl)clavulanate

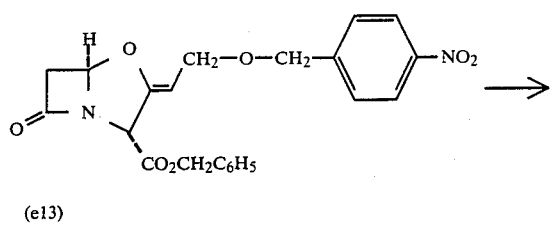

(e13)

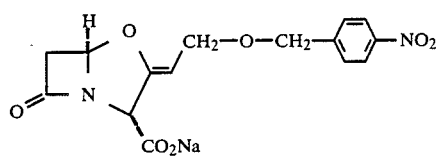

(e21)

A solution of benzyl 9-[O-(4-nitrobenzyl)]clavulanate (e13) (110 mgs) and sodium bicarbonate (21.7 mgs) in tetrahydrofuran, water (5:1, 8 mls) was hydrogenated over 10% palladium charcoal (68 mgs) for 15 minutes. The solution was filtered through celite, and the solid was washed with water. The combined filtrates were evaporated to remove most of the tetrahydrofuran, and the remaining aqueous solution was washed with ethyl acetate. The aqueous solution was then evaporated and the residual gum was purified by column chromatography (Kieselgel H, N-butanol:water-ethanol, 4:1:1 as eluant) to give the produce (e21) (39 mgs) as a yellow solid (estimated 70% pure).

I.R. (KBr) 1790, 1605 (broad) cm−1 N.m.r. (DMSO) 2.83 (IH, doublet, J 17 Hz) 3.41 (IH,double doublet, J 17 Hz and 3 Hz) 3.88 (2H, doublet, J 7 Hz), 4.4 (2H, singlet), 4.52 (IH singlet), 4.67 (IH, multipet), 5.57 (IH, singlet with fine coupling), 6.46 (2H, doublet J 9 Hz), 6.89 (2H, doublet, J 9 Hz).

EXAMPLE 23

Preparation of Benzyl 9-O-(3'-hydroxypropyl)clavulanate

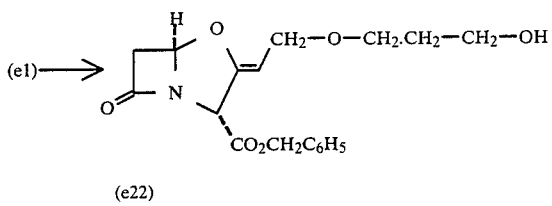

(e22)

(i) N,O-bis-(benzyloxycarbonyl)-3-aminopropanol

Benzyl chloroformate (47 ml.) was added dropwise to a stirred solution of 3-aminopropanol (11.4 ml) in pyridine (150 ml) at 0°. The mixture was then stirred at room temperature overnight. This was poured into ice-water (300 ml.) and extracted with ethyl acetate (3×200 ml). The organic extract was washed with hydrochloric acid (5 m, 3×400 ml), dried with anhydrous sodium carbonate-magnesium sulphate and evaporated to give the desired compound as an oil contaminated with a little dimethylcarbonate (30.23 g).

(ii) N-Nitroso-N,O-bis-(benzyloxycarbonyl)-3-Aminopropanol

Anhydrous sodium acetate (45 g) was added to carbon tetrachloride (150 ml) at 0° and the mixture was cooled to −20° which was then added to a solution of nitrogen dioxide (24.1 g) in carbon tetrachloride (150 ml). A solution of N,O-bis-(benzyloxycarbonyl)-3-aminopropanol (30.23 g) in carbon tetrachloride (150 ml) was added to the stirred mixture at −5° which was then stirred at 0° for 0.5 of an hour. The reaction mixture was washed with aqueous sodium bicarbonate (2×400 ml), dried, and evaporated to give the desired compound as an oil (31.23 g), $\nu_{max}$ (liquid film) 1750, 1510, 1400, 1260, 1125 and 1035.

(iii) Benzyl 9-O-(3'-benzyloxycarbonyloxypropyl)clavulanate

Pyrrolidine (4.94 ml) was added to a solution of N-nitrose-N,O-bis-(benzyloxycarbonyl)-3-aminopropanol (31.22 g, 0.056 mole in the mixture) in methylene chloride (100 ml) at −20° for 15 minutes to give a solution of 3-diazo-O-benzyloxycarbonylpropanol, $\nu_{max}$ (CH$_2$Cl$_2$) 2030 cm−1. This solution was kept at 0° for the next stage.

Boron trifluoride etherate (1 ml) was added to a solution of benzyl clavulanate (3 g) in methylene chloride (150 ml) at −30°. The solution of 3-diazo-O-benzyloxycarbonylpropanol prepared above was added to the mixture at −30° and the solution was stirred at −30° to −10° for 1 hour. This was washed with aqueous sodium bicarbonate (2×200 ml) dried, and evaporated to give an oil which was chromatographed on silica gel (80 g). Elution of the column with Cyclohexaneethyl acetate afford the title compound (e22) (1.5 g), δ(CDCl$_3$) 7.36 (10H, s, ArH), 5.70 (IH,d, J=2.5 Hz, 5-CH), 5.18 (4H,s, CH$_2$Ph), 5.13 (IH, m, 3-CH), 4.84 (IH, broad t, J=8 Hz, 8-CH), 4.26 (IH, t, J=6 Hz, CH$_2$CH$_2$OCBz), 4.06 (IH, d, J=8 Hz, 9-CH$_2$), 3.60–3.26 (4H, m, O—CH$_2$CH$_2$ and 6α-CH), 3.02, (IH, d, J=18 Hz, 6β-CH), and 1.86 (IH, m, CH$_2$CH$_2$CH$_2$).

EXAMPLE 24

Preparation of Sodium 9-O-(3'-hydroxypropyl)clavulanate

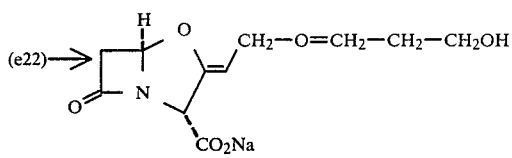

A mixture of benzyl 9-O-(3-benzyloxycarbonyloxypropyl)clavulanate (0.5 g) and sodium carbonate (0.05 g) in tetrahydrofuran-water (5:1, 12 ml) was hydrogenated at room temperature and pressure in the presence of 10% palladium-charcoal (0.3 g) for 15 minutes. The mixture was filtered and the filtrate evaporated to give an oil which was partitioned between water and ethyl acetate. The aqueous fraction was freeze dried to give the title compound with a consistent n.m.r. spectrum.

EXAMPLE 25

9-O-[2'-(N,N-dimethyl)aminoethyl]clavulanate

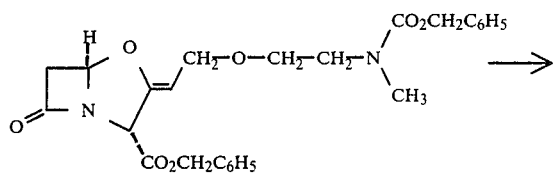

A solution of the benzyl ester (e20) (90 mgs) in tetrahydrofuran (5 ml) and water (1 ml) was hydrogenated over 10% palladium charcoal (30 mgs) for 15 minutes. The catalyst was filtered off and washed with water. The combined filtrates were evaporated to remove the tetrahydrofuran and the aqueous solution was then extracted twice with ethyl acetate. The aqueous solution was evaporated and the residue purified by column chromatography (Whatman cellulose powder CC31 with butanol:water:ethanol, 4:1:1 as eluant) to yield the desired product (e24) (15 mg).

I.r. (CHCl$_3$): 1790 and 1620 cm$^{-1}$.

N.m.r. (D$_2$O) consistent with assigned formula.

EXAMPLE 26

Sodium 9-O-allylclavulanate

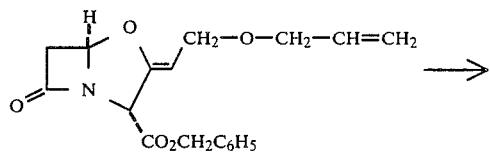

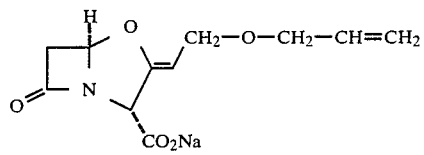

A solution of benzyl 9-O-allylclavulanate (e14) (0.5 g) in tetrahydrofuran-water (1:4, 30 ml) was titrated to constant pH at pH 10 with aqueous sodium hydroxide at room temperature. The reaction mixture was diluted with water (30 ml) and the neutral organic material was removed by continuous extraction with ether. The aqueous solution was freeze-dried and then chromatographed over silica gel. Elution of the column with butanol-ethanol-water (4:1:1.75) gave the title compound (e25) (0.01 g).

N.m.r. (D$_2$O): 5.63 (1H, d, J 3 Hz, 5-C$\underline{H}$), 4.97–5.40 (3H, m, —C$\underline{H}$=C$\underline{H}_2$), 4.87 (1H, m, 3-C$\underline{H}$), 4.83 (1H, broad t, J 8 Hz, 8-C$\underline{H}$), 4.19 (2H, d, J 8 Hz, 9-C$\underline{H}_2$), 3.91 (2H, broad d, J 6 Hz, —C$\underline{H}_2$CH=CH$_2$), 3.49 (1H, dd, J 18 Hz, J' 3 Hz, 6α-C$\underline{H}$), and 2.97δ (1H, d, J 18 Hz, 6β-C$\underline{H}$).

EXAMPLE 27

Preparation of p-Methoxybenzyl-9-O-ethoxycarbonylmethylclavulanate

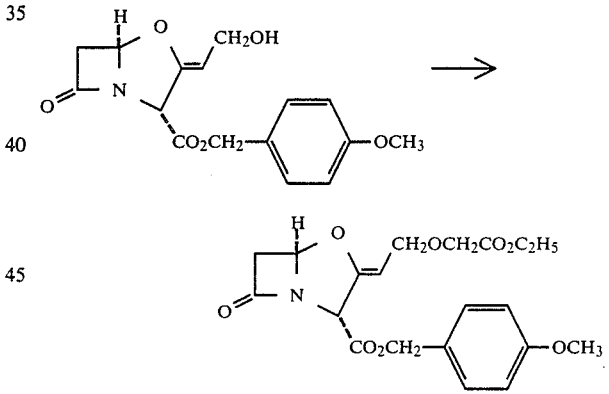

A solution of p-methoxybenzyl clavulanate (9.6 g) in dry dichloromethane (200 ml) was stirred at −30° C. Re-distilled BF$_3$-ether complex (1 ml) was added, followed by ethyl diazoacetate (16 ml). The temperature was allowed slowly to rise to −10° C., and then stirred for 3 hours at that temperature. Saturated aqueous sodium bicarbonate solution (2×200 ml portions) was added, shaken, separated, the organic layer being retained. It was dried over MgSO$_4$, filtered and evaporated to a syrup, which was subjected to column chromatography over silica gel, eluting with ethyl acetate and cyclohexane graded from 1:3 to 1:2 ratio. Fractions containing the product (by thin layer chromatography) were combined and evaporated, to yield the desired material (5.5 g).

I.r. 1805 (β-lactam C═O), 1750 (ester C═O), 1700 cm$^{-1}$ (C═C), (film).

EXAMPLE 28

Preparation of Lithium 9-O-ethoxycarbonylmethyl clavulanate

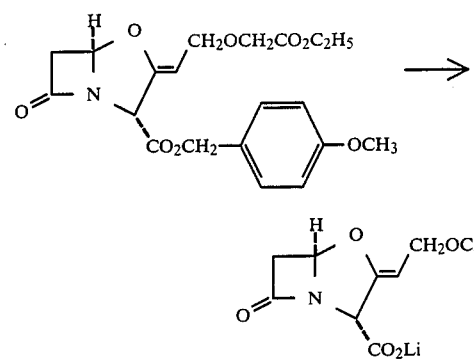

p-Methoxybenzyl O-ethoxycarbonylmethyl clavulanate (4 g) in re-distilled tetrahydrofuran (40 ml) containing water (0.1 ml) was hydrogenated over 10% palladised charcoal (1.2 g) for 30 minutes at room temperature, when thin layer chromatography showed that the starting material had disappeared. The catalyst was removed by filtration, the filtrate added to water (50 ml) and titrated to pH 7.0 with 1.0M lithium hydroxide solution (required 7.5 ml, theory 10 ml, short fall due to solvent in starting material). The solution was evaporated to a pale yellow syrup in vacuo, and the residue triturated with acetone (50 ml) when it crystallized. It was collected, washed with acetone and with ether, and air-dried, to yield 1.6 g of almost colourless crystalline solid.

I.r. 1795 ($\beta$-lactam C=O), 1735 (ester C=O), 1695 (C=C), 1620 cm$^{-1}$ (CO$_2^-$), nujol mull.

EXAMPLE 29

Preparation of Sodium 9-O-ethoxycarbonylmethylclavulanate

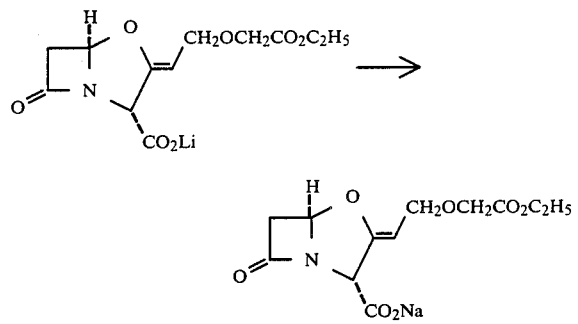

The lithium salt (1.2 g) was dissolved in water (5 ml) and passed through a column of Amberlite IR-120 (Na$^+$) (25 ml wet resin), standard grade. The sodium salt was washed through with 100 ml (total) of distilled water. (The proportion of the compound remaining as Li$^+$ salt was 0.5% by atomic emission spectroscopy). The eluate was evaporated to dryness under vacuum, and the residual gum triturated with acetone and ether to yield 0.98 g of the product as an off-white crystalline solid.

I.r. (n/m) 3400 (H$_2$O), 1795 ($\beta$-lactam C=O), 1745 (ester C=O), 1695 (C=C), 1620 cm$^{-1}$ (CO$_2^-$).

EXAMPLE 30

Preparation of Phthalidyl 9-O-ethoxycarbonylmethylclavulanate

Lithium O-ethoxycarbonylmethyl clavulanate (0.7 g) was dissolved in dimethylformamide (10 ml), stirred at room temperature and 3-bromophthalide (0.5 g) added, dissolved in dimethylformamide (2 ml). After 1 hour at ambient temperature (~20° C.) thin layer chromatography showed the reaction was virtually complete. The solution was evaporated to low volume in vacuo, treated with 1:1 cyclohexane-ethyl acetate (50 ml), washed with water (10 ml) and the solvent layer dried over sodium sulphate. The solvents were evaporated to small volume under reduced pressure, and the residue subjected to rapid column chromatography on silica gel, using ethyl acetatecyclohexane (1:1) as eluent. The fractions containing the product (by thin layer chromatography) were evaporated, triturated with dry ether to remove insoluble phthalide-derived impurities (0.04 g), and evaporated, to yield the compound as a colourless oil (0.25 g).

I.r. (film) 1742-1800 ($\beta$-lactam, lactone, ester C=O), 1698 cm$^{-1}$ (C=C);

N.m.r. (CDCl$_3$) 1.27 (3H, t, J 7.5 Hz, CH$_2$C$\underline{H}_3$), 3.02 (1H, d, J 17 Hz, 6-$\beta$-C$\underline{H}$), 3.44 (1H, dd, J 17 and 3 Hz, 6-$\alpha$-C$\underline{H}$), 3.90-4.25 (6$\underline{H}$, br.m., OC$\underline{H}_2$CO, C$\underline{H}_3$CH$_2$, =CHC$\underline{H}_2$), 4.82 (1H, t, J 7 Hz, =C$\underline{H}$), 5.08 (1$\underline{H}$, $\delta$, 3-C$\underline{H}$), 5.61 (1H, d, J 3 Hz, 5-C$\underline{H}$), 7.33 (1H, s, phthalide 3-C$\underline{H}$), 7.45-7.9 $\delta$ (4H, m, phthalide C$_6\underline{H}_4$).

EXAMPLE 31

Preparation of Lithium 9-O-butylclavulanate

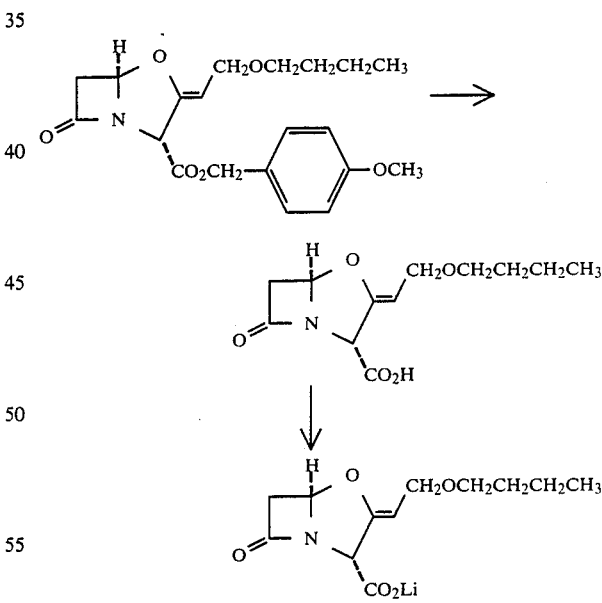

A solution of p-methoxybenzyl 9-O-butylclavulanate (80 mg) in tetrahydrofuran (6 ml) containing water (0.02 ml) was hydrogenated over 10% palladised charcoal (40 mg) for 15 minutes, when thin layer chromatography showed the absence of starting material. The catalyst was removed by filtration to yield a solution of clavulanyl butyl ether. This solution was diluted with water (20 ml) and titrated to pH 7.5 with 0.1M lithium hydroxide solution. The solution was evaporated to a semi-solid residue in vacuo, the residue triturated with acetone, filtered off, washed with ether and air-dried, to yield 40 mg of crystalline lithium 9-O-(n-butyl)clavulanate.

I.r. (Nujol mull) 1768 (β-lactam C=O), 1698 (C=C), 1618 cm⁻¹ (CO₂⁻);

N.m.r. (D₂O)δ0.73 (3H, t, J 7 Hz, (CH₂)₃CH₃), 0.95-1.60 (4H, m, CH₂CH₂C₃), 2.94 (1H, d, J 17 Hz, 6-β-CH), 3.36 (2H, t, J 7 Hz, OCH₂CH₂), 3.43 (1H, dd, J 17 and 3 Hz, 6-α-CH), 3.97 (2H, d, J 8 Hz, =CHCH₂), 4.76 (1H, t, J 8 Hz, CH=), 4.84 (1H, s, 3-CH), 5.99 (1H, d, J 3 Hz, 5-CH).

EXAMPLE 32

Preparation of p-Methoxybenzyl 9-O-butylclavulanate

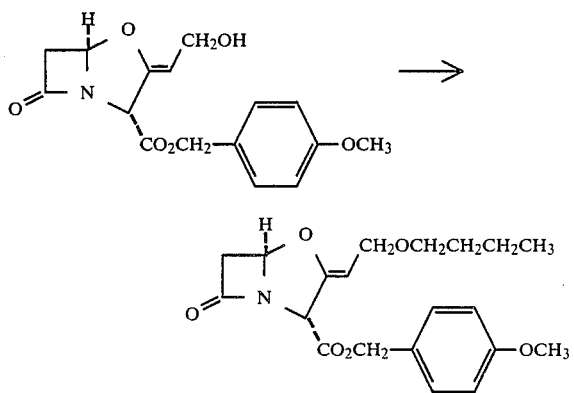

Di-n-butyl ether (1.63 ml), 1-bromobutane (1.43 ml) and 1M silver tetrafluoroborate solution in 1,2,-dichloroethane (5.0 ml) were mixed and set aside for 1 hour at 20° C. The precipitated AgBr was filtered off, and washed with dichloromethane (2 ml). The filtrate was cooled to −20° C. and successively anhydrous sodium carbonate (1 g) and a solution of p-methoxybenzyl clavulanate (0.5 g) in dichloromethane (5 ml) were added with efficient stirring. After 48 hours at −20° C. (without stirring) and a total of 6 hours at room temperature, the insoluble material was filtered off, the filtrate washed with water (10 ml), dried over anhydrous sodium sulphate and evaporated to a gum, which was subjected to chromatography over silica gel, eluting with 1:3 ethyl acetate/cyclohexane. After evaporation of the solvents, the butyl ether of p-methoxybenzyl clavulanate was obtained as an almost colourless oil, 80 mg yield.

I.r. (film) 1805, 1745, 1695 cm⁻¹;

N.m.r. 0.89 (3H, t, J 6.5 Hz, CH₃CH₂—), 1.1-1.8 (4H, m, CH₂CH₂CH₃), 2.96 (1H, d, J 17 Hz, 6-β-CH), 3.31 (2H, t, J 6.5 Hz, OCH₂CH₂), 3.39 (1H, dd, J 17 and 3 Hz, 6-α-CH), 3.74 (3H, s, OCH₃), 3.97 (2H, d, J 7 Hz, =CHCH₂), 4.75 (1H, dt, J 1.5 and 7 Hz, =CH), 4.99 (1H, s, 3-CH), 5.06 (2H, s, C₆H₄CH₂), 5.58 (1H, d, J 3 Hz, 5-CH), 6.79, 7.19δ (4H, A₂B₂q, J 9 Hz, C₆H₄).

EXAMPLE 33 p-Methoxybenzyl 9-O-ethylclavulanate

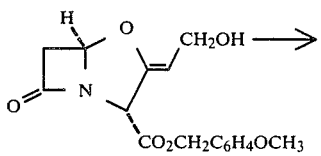

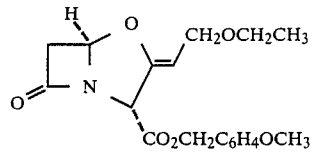

To a solution of p. methoxybenzyl clavulanate (9.6 g, 0.03 mole) in dichloromethane (500 ml) stirred at −30° C., was added successively anhydrous sodium carbonate (15 g, excess) and a solution of triethyloxonium tetrafluoroborate (17.6 g, 0.09 mole) in dichloromethane (100 ml).

The mixture was stirred at about −10° C. for 6 hr, then allowed to warm to ambient temperature during ½ hr. Water (100 ml) was added cautiously with stirring, the organic phase separated, dried over anhydrous sodium sulphate, and evaporated to a syrup. This was subjected to column chromatography on silica gel, eluting initially with 1:1, then with 2:1, ethylacetate-cyclohexane mixtures. The first eluted product was the ethyl ether (4.9 g after evaporation of solvents) followed by recovered p-methoxybenzyl clavulanate (4 g). The ethyl ether was a pale yellow oil with the following properties.

I.r. (liquid film) 1805 (β-lactam C=O) 1750 (ester C=O) 1700 cm⁻¹ (C=C); part nmr (CDCl₃) 1.17 (3H, t, J 7 Hz, CH₃CH₂) 2.96 (1H, d, J 17 Hz, 6-β-CH) 3.41 (2H, q, J 7 Hz, CH₃CH₂—) 3.47 (1H, dd, J 17 and 3 Hz, 6-α-CH) 3.79 (3H, s, OCH₃) 4.03 (2H, d, J 7 Hz, —CH₂O) 4.82 (1H, t, J 7 Hz, CH=) 5.04 (1H, s, 3-CH) 5.11δ(2H, s, PhCH₂)

EXAMPLE 34

Lithium 9-O-ethylclavulanate

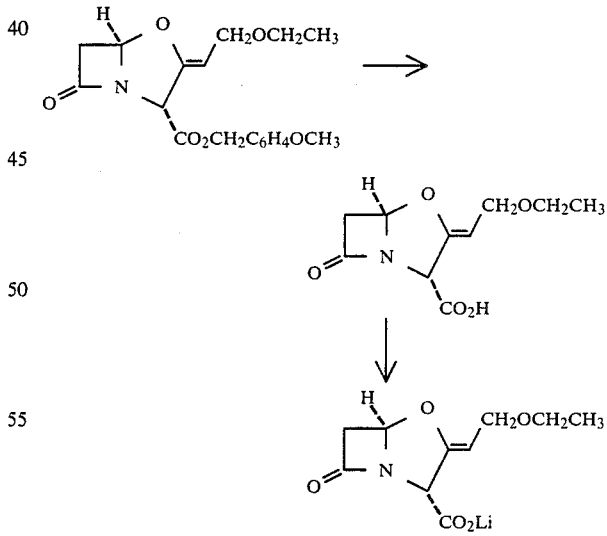

p-Methoxybenzyl 9-O-ethylclavulanate (2.5 g) in tetrahydrofuran (25 ml) containing water (0.1 ml) was hydrogenated over 10% palladised charcoal (0.8 g). After 2 hr, the absence of starting material was demonstrated by tlc. The catalyst was removed by filtration through a bed of finely divided silica, the filtrate diluted with an equal volume of water and titrated to pH 7.0 with 1M lithium hydroxide solution. Evaporation of the solvents and trituration with acetone yielded the lithium salt as a pale cream crystalline solid (1.05 g).

(The sodium salt was prepared in an identical manner using 1M NaOH solution; yield 0.85 g). Properties of lithium salt. I.r. (nujol mull) 1785 (β-lactam C═O) 1685 (C═C) 1615 cm$^{-1}$ (—CO$_2$—).

EXAMPLE 35

Preparation of Crystalline Lithium 9-O-methylclavulanate

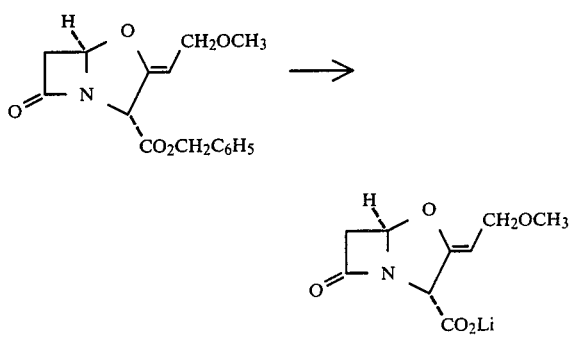

Benzyl 9-O-methylclavulanate (0.52 g) and lithium carbonate (0.063 g) in ethanol-water (6:1, 17 ml) and hydrogenating the mixture at room temperature and atmospheric pressure over 10% palladium charcoal (0.2 g) for 30 minutes at the end of which time the mixture was filtered, concentrated by evaporation and freeze dried to yield an amorphous solid. This was dissolved in water (about 1 ml) and to this solution was added acetonitrile (about 30 ml). The mixture was cooled in an ice bath and scratched until crystallisation commenced (about 30 minutes). The colourless solid was filtered off and dried to the desired lithium clavulanyl O-methyl ether as microcrystals (0.13 g).

EXAMPLE 36

Preparation of Crystalline Sodium 9-O-methylclavulanate (a) Amorphous sodium 9-O-methylclavulanate (500 mg) was added to ethyl acetate (50 ml) and the mixture gently boiled for 5 minutes. The solution was filtered hot and the filtrate allowed to cool to room temperature when crystals appeared. When crystallisation appeared complete the crystals were filtered off and dried in dry air to yield the desired crystalline sodium 9-O-methylclavulanate.

(b) Amorphous sodium 9-O-methylclavulanate (100 mg) was dissolved in hot acetone (4 ml). The solution was filtered and the filtrate allowed to cool to room temperature. To this was added ether (about 20 ml) dropwise until crystals appeared. The suspension was boiled to dissolve the crystals and then allowed to cool. After cooling in an ice bath and scratching for a few minutes the desired crystalline materials formed and was collected by filtration to yield fine crystals.

EXAMPLE 37 p-Methoxybenzyl 9-O-Ethylclavulanate

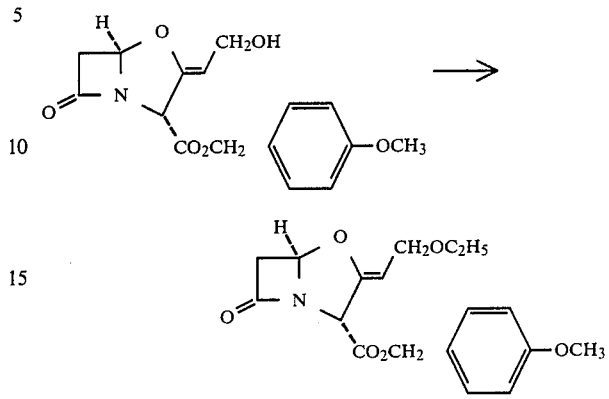

A mixture of p-methoxybenzyl clavulanate (3.19 g), powdered calcium oxide (4.0 g), silver oxide (4.0 g), and ethyl iodide (6 ml) in benzene (50 ml) was boiled under reflux for 2 h. The cooled reaction mixture was filtered and the filtrate evaporated to give an oil which was chromatographed over silica gel (30 g). Elution of the column with ethyl acetate-cyclohexane (1:4) afforded the title compound (0.74 g) in pure form identical to an authentic sample (ir. and $^1$H n.m.r. comparisons).

A similar result may be obtained by replacing the ethyl iodide with ethyl bromide and carrying out the reaction at 40° C. for a longer period.

The corresponding methyl ether can also be prepared by substituting methyl iodide for the above ethyl iodide.

EXAMPLE 38 p-Methoxybenzyl 9-O-Benzylclavulanate

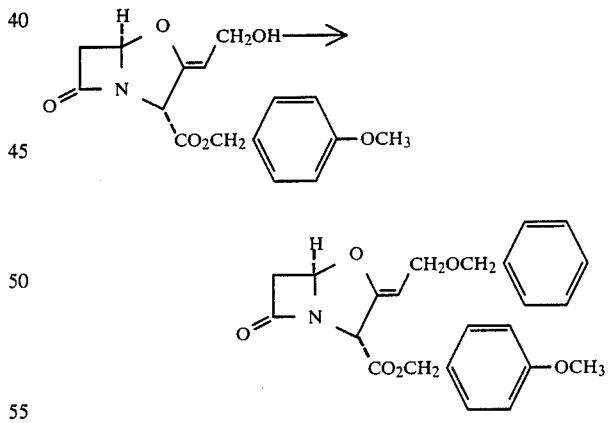

A mixture of p-methoxybenzyl clavulanate (3.19 g), powdered calcium oxide (4.0 g), silver oxide (4.0 g) and benzyl bromide (5 ml) in benzene (50 ml) was boiled under reflux for 2 h. The cooled reaction mixture was filtered and the filtrate evaporated to give an oil which was chromatographed over silica gel (30 g). Elution of the column with ethyl acetate-cyclohexane (1:4) afforded the title compound (1.0 g), $\nu_{max}$ (liquid film) 1810, 1750, 1700, 1310, 1250, 1180 and 1040 cm$^{-1}$, δ (CDCl$_3$) 7.22 (5H, s, ArH), 7.19 (2H, d, J=9 Hz, ArH), 6.76 (2H, d, J=9 Hz, ArH), 5.58 (1H, d, J=2.5 Hz, 5-CH), 5.08 (2H, s, —CH$_2$Ar), 5.00 (1H, broad s, 3-CH), 4.80 (1H, broad t, e,uns/J/ =8 Hz, 8-C$\underline{H}$), 4.38 (2H, s, —C$\underline{H_2}$Ar), 4.05 (2H, broad d, J=8 Hz, 9-C$\underline{H_2}$), 3.70 (3H, s, OC$\underline{H_3}$), 3.40 (1H, dd, $\underline{J}$=17 Hz, J'×2.5 Hz, 6α-C$\underline{H}$), and 2.96 (1H, d, $\underline{J}$=17 Hz, 6β-C$\underline{H}$).

EXAMPLE 39 p-Methoxybenzyl 9-O-Allylclavulanate

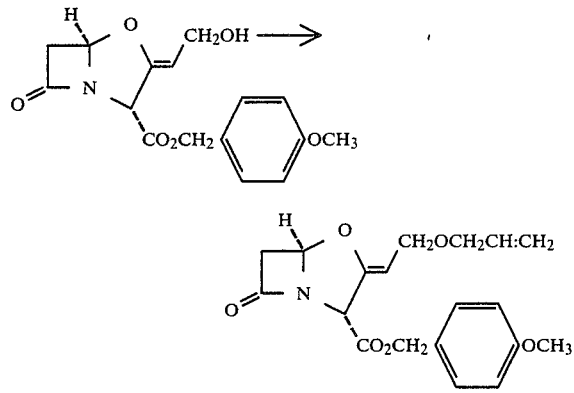

A mixture of p-methoxybenzyl clavulanate (3.19 g), powdered calcium oxide (4.0 g), silver oxide (4.0 g), and allyl bromide (4 ml) in benzene (30 ml) was stirred at room temperature for 66 h. The mixture was filtered and the filtrate evaporated to give an oil which was chromatographed over silica gel (20 g). Elution of the column with cyclohexane-ethyl acetate (4:1) afforded the title compound (0.65 g), $\nu_{max}$ (liquid film) 3020, 1810, 1750, 1700, 1310, 1255, 1080 and 1040 cm$^{-1}$, δ (CDCl$_3$) 7.30 (2H, d, J=9 Hz, Ar$\underline{H}$), 6.86 (2H, d, J=9 Hz, Ar$\underline{H}$), 5.95 (1H, m, C=C$\underline{H}$), 5.67 (1H, d, J=2.5 Hz, 5-C$\underline{H}$), 5.32 (2H, m, C=C$\underline{H}$), 5.13 (2H, s, —C$\underline{H_2}$Ar), 5.06 (1H, s, 3-C$\underline{H}$), 4.83 (1$\underline{H}$, broad t, J=8 Hz, 8-C$\underline{H}$), 4.06 (2H, broad d, J=8 Hz, 9-C$\underline{H_2}$), 3.92 (2H, m, —OC$\underline{H_2}$—CH=CH$_2$), 3.80 (3H, s, OC$\underline{H_3}$), 3.50 (1H, dd, $\underline{J}$=17 Hz, J'=2.5 Hz, 6α-C$\underline{H}$), and 3.00 (1H, d, $\underline{J}$=17 Hz, 6β-C$\underline{H}$).

EXAMPLE 40

Benzyl 9-O-methylclavulanate

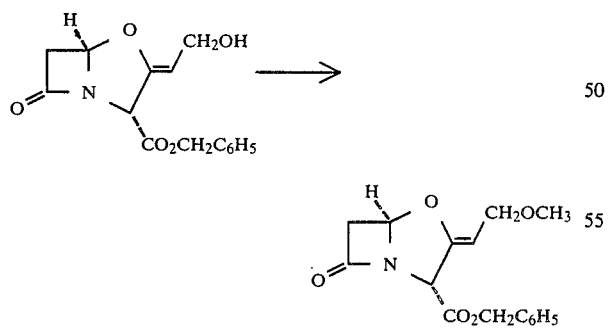

A mixture of benzyl clavulanate (8.67 g), calcium oxide (12 g), silver oxide (12 g) and methyl iodide (15 ml) in benzene (50 ml) was heated under reflux for 2 hours. The mixture was allowed to cool, was filtered and the filtrate evaporated to give an oil which was chromatographed over silica gel (50 g) eluting with ethyl acetate/cyclohexane (1:4) to give the title compound (2.81 g).

EXAMPLE 41

Benzyl 9-O-Nonylclavulanate

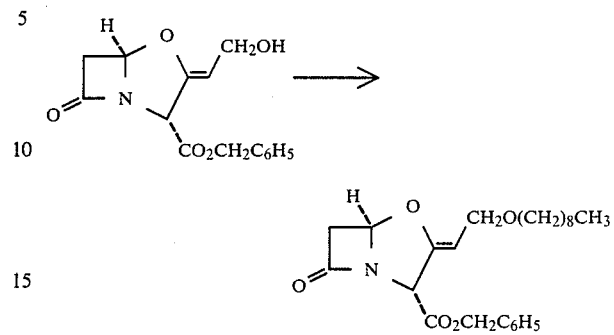

Benzyl clavulanate (2.89 g) in ethyl acetate (10 ml) and iodononane (12.7 g) were heated under reflux with stirring in presence of silver oxide (4 g) and calcium oxide (4 g) for 3 hours. Tlc showed a fastrunning zone and a much diminished zone due to starting material. The mixture was filtered, the insolubles washed with ethyl acetate (50 ml) and the filtrate evaporated under reduced pressure to a dark oil. This was subjeted to column chromatography on silica gel, using ethyl acetate and cyclohexane graded from 1:10 to 1:2 as eluents. Fractions after the nonyl iodide had been eluted contained the product, which was isolated as a pale yellow oil by evaporation of the solvents; yield 0.64 g. Ir. (l/f): 1805, 1750, 1695 cm$^{-1}$.

n.m.r. (CDCl$_3$) δ: 0.86 (3H, t, J 7 Hz, C$\underline{H_3}$), 1.25 (14H, m, O—CH$_2$(C$\underline{H_2}$)$_7$CH$_3$), 2.98 (1$\underline{H}$, d, J 17 Hz, 6-β-C$\underline{H}$), 3.31 (2H, t, $\underline{J}$ 7 Hz, OC$\underline{H_2}$(CH$_2$)$_7$), 3.43 (1H, dd, J 17 Hz and 3 Hz, 6-α-C$\underline{H}$), 3.98 (2H, d, J 7 Hz, C$\underline{H_2}$CH=), 4.78 (1H, t, J 7 Hz, C$\underline{H}$=), 5.02 (1$\underline{H}$, s, 3-C$\underline{H}$), 5.12 (2H, s, PhC$\underline{H_2}$), 5.61 (1$\underline{H}$, d, $\underline{J}$ 3 Hz, 5-C$\underline{H}$) and 7.27 (5H, s, C$_6$$\underline{H_5}$).

Using the method of Example 56 the ester (0.6 g) was converted to the crystalline lithium salt (0.22 g).

I.r. 1775, 1695, 1620 cm$^{-1}$.

EXAMPLE 42

DL-Benzyl 9-O-(but-2-yl)clavulanate

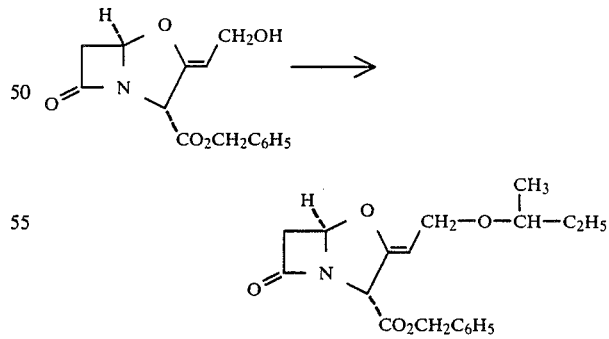

Benzyl clavulanate (2.89 g) in ethyl acetate (7 ml) and 2-iodobutane (9 g) were refluxed with stirring in the presence of silver oxide (4 g) and calcium oxide (4 g) for 2½ hr. The insoluble materials were filtered off, and the filtrate concentrated in vacuo to a yellow oil, which was subjected to column chromatography on silica gel using ethyl acetate and cyclohexane graded from 1:10 to 1:2 ratio. The ether was eluted after the 2-iodobutane.

Fractions containing the ether (by tlc) were evaporated in vacuo to yield the compound (0.57 g) as a pale yellow oil.

I.r. (l/f) 1808, 1753, 1698 cm⁻¹.

Nmr (CDCl₃) δ 0.84 (3H, t, J 7 Hz, CH₂C$\underline{H}$₃), 1.07 (3H, d, J 7 Hz, CH—C$\underline{H}$₃), 1.26–1.63 (2H, m, C$\underline{H}$₂CH₃), 2.96 (1H, d, J 17 Hz, 6-β-C$\underline{H}$), 3.26 (1H, qt, J 7 Hz OC$\underline{H}$), 3.41 (O$\underline{H}$, dd, J 17 Hz, 3 Hz, 6-α-C$\underline{H}$), 3.8–4.25 (1$\underline{H}$, m, 9-C$\underline{H}$₂), 4.77 (1H, t, J 8 Hz 8-C$\underline{H}$), 5.20 (1H, s, 3-C$\underline{H}$), 5.12 (2H, s, CH₂Ph), 5.90 (1H, d, J 3 Hz, 5-C$\underline{H}$) 7.28 (5H, s, C₆$\underline{H}$₅).

A repetition using 8 g of silver oxide in place of 4 g of silver oxide plus 4 g calcium oxide yielded 0.8 g of the same product.

EXAMPLE 43

Benzyl 9-O-t-Amyl clavulanate

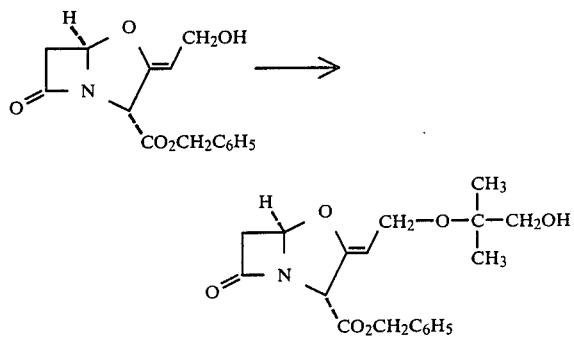

Benzyl clavulanate (2.89 g) in ethyl acetate (20 ml) and 2-iodo-2-methylbutane (6.5 ml, 9.9 g) was stirred at room temperature in the presence of silver oxide (4 g) and calcium oxide (4 g) for 3 hr. The insoluble material was filtered off, washed with ethyl acetate (50 ml) and filtrate evaporated under reduced pressure to a dark oil, which was subjected to column chromatography on silica gel, eluting with cyclohexane-ethyl acetate graded from 10:1 to 3:1, to yield 0.43 g of the title product as a pale yellow oil.

I.r. 1805, 1755, 1698 cm⁻¹; (liquid film). nmr. (CDCl₃) δ 0.83 (3H, t, J 7 Hz, CH₂C$\underline{H}$₃), 1.11 (6H, s, (CH₃)₂), 1.46 (2H, q, J 7 Hz, C$\underline{H}$₂CH₃), 2.96 (1H, d, J 17 Hz, 6-β-C$\underline{H}$), 3.40 (1H, dd, J 17 and 3 Hz, 6-α-CH), 3.6–4.3 (2$\underline{H}$, m, =CHC$\underline{H}$₂), 4.74 (1H, dt, J 7 and ~2 Hz, C$\underline{H}$=), 5.0 (1H, d, J ~2 Hz, 3-C$\underline{H}$), 5.12 (2H, s, PhC$\underline{H}$₂), 5.59 (1H, d, J 3 Hz, 5-C$\underline{H}$), 7.27 (5H, s, C₆$\underline{H}$₅).

EXAMPLE 44

Preparation of Benzyl 9-O-phenacylclavulanate

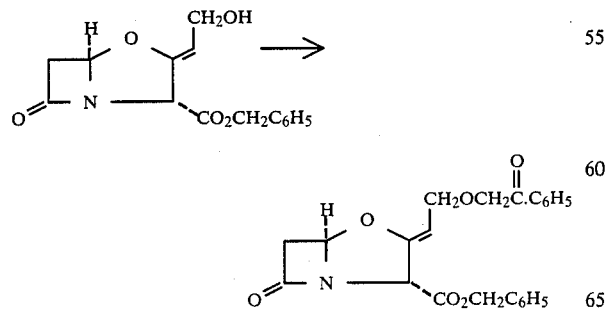

Benzyl clavulanate (0.83 g) and diazoacetophenone (1.45 g) were dissolved in methylene chloride (20 ml) and stirred at −20° C. Boron trifluoride diethyletherate (0.15 ml) was added and the solution stirred at −10° C. for 2.0 hours. The reaction was quenched with dilute bicarbonate solution. The organic extract was washed with bicarbonate solution, sodium chloride solution, and then dried over MgSO₄. The product (206 mg) was isolated as a colourless oil, after chromatography twice over silica gel (eluting ethyl acetate/petrol). ν$_{max}$ (CHCl₃); 1805, 1735–1755, 1705 cms⁻¹; δ (CDCl₃) 2.97 (1H, d, J 17 Hz, 6β-C$\underline{H}$), 3.47 (1H, dd, J 17 Hz, J' 2.5 Hz, 6α-C$\underline{H}$), 4.28 (2H, d, J 7 Hz, 9-C$\underline{H}$₂), 4.72 (2H, s, —OC$\underline{H}$₂CO), 4.93 (1H, t, J 7 Hz, 8-C$\underline{H}$), 5.17 (1H, s, 3-C$\underline{H}$), 5.26 (2H, s, CO₂C$\underline{H}$₂Ph), 5.70 (1H, d, J 2.5 Hz, 5-C$\underline{H}$), 7.35–8.10 (10H, m, aryl).

EXAMPLE 45

Preparation of Allyl 9-O-acetonylclavulanate

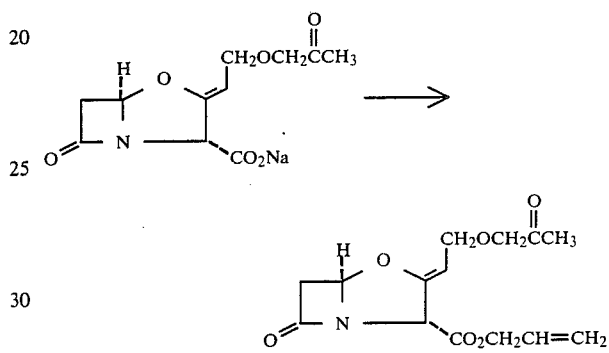

The sodium salt (20 mg) was dissolved in dry DMF (2 ml) and stirred with excess allyl bromide, overnight. The solution was taken to dryness on a rotary evaporator and then partitioned between ethyl acetate and water. The ethyl acetate solution was dried, filtered and evaporated. The product (7.1 mg) was isolated as a clear oil by column chromatography over silica gel (eluting ethyl acetate/petrol). ν$_{max}$ (CHCl₃) 1805, 1720–1750, 1705 cms⁻¹ δ (CDCl₃) 2.10 (3H, s, —C$\underline{H}$₃), 3.00 (1H, d, J 17 Hz, 6β-$\underline{H}$), 3.45 (1H, dd, J 17 Hz, J' 2 Hz, 6α-C$\underline{H}$), 3.93 (2H, s, OC$\underline{H}$₂CO), 4.08 (2$\underline{H}$, d, J 7 Hz, 9-C$\underline{H}$₂), 4.57 (2H, d, J 7 Hz, CO₂C$\underline{H}$₂), 4.80 (1$\underline{H}$, t, J 7 Hz, 8-C$\underline{H}$), 5.02 (1H, s, 3-C$\underline{H}$), 5.27 (2H, m, =C$\underline{H}$₂), 5.64 (1H, d, J 2 Hz, 5-C$\underline{H}$), 5.70–6.0 (1$\underline{H}$, m, CH₂—C$\underline{H}$=CH₂).

EXAMPLE 46

Preparation of Allyl 9-O-(p-chlorophenacyl)clavulanate

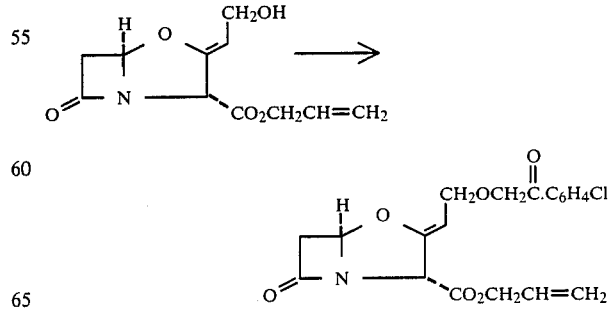

Allyl clavulanate (0.55 g) and α-diazo-p-chloroacetophenone (0.77 g) were dissolved in methylene chloride (25 ml). Boron trifluoridediethylethereate (25 drops) was added and the solution stirred at $-20°$ to $-10°$ C. for 2.0 hours. The reaction was quenched with dilute sodium hydroxide solution and the separated organic layer washed with water. The solution was dried over $Na_2SO_4$, filtered and evaporated. Chromatography over silica gel (eluting with chloroform) yielded the product (200 mg); $\nu_{max}$(CHCl$_3$) 1800, 1745, 1690 1590 cm$^{-1}$; δ (CDCl$_3$); 2.94 (1H, d, J 17 Hz, 6β-C$\underline{H}$), 3.42 (1H, dd, J 17 Hz, J' 2.5 Hz, 6α-C$\underline{H}$), 4.17 (2H, d, J 7 Hz, 9-CH$_2$), 4.72 (2H, s, OC$\underline{H_2}$CO), 4.57 (2H, d, J 6 Hz, CO$_2$C$\underline{H_2}$), 4.82 (1H, t, J 7 Hz, 8-C$\underline{H}$), 5.02 (1H, s, 3-C$\underline{H}$), 5.25 (2H, m, =C$\underline{H_2}$), 5.61 (1$\overline{H}$, d, J 2.5 Hz, 5-C$\underline{H}$), 5.6–6.1 (1H, m. C$\underline{H_2}$—C$\underline{H}$=CH$_2$), 7.2–7.85 (4H, m, aryl).

EXAMPLE 47

Preparation of Sodium 9-O-[(2'-hydroxy-2'-phenyl)ethyl]clavulanate

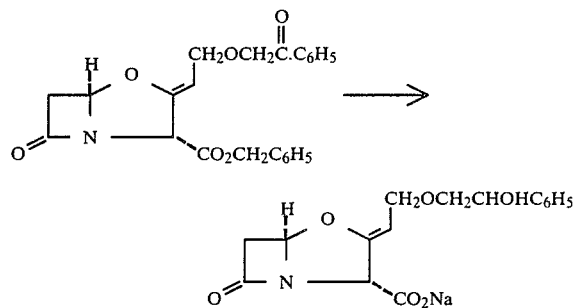

To a 25 ml RB flask was added the phenacyl ether (150 mg), 10% palladium/carbon (50 mg), tetrahydrofuran (5 ml), water (1 ml) and sodium bicarbonate (30 mg). The solution was hydrogenated at atmospheric pressure and temperature, with shaking, for thirty minutes. The solution was filtered and washed with a little water. The aqueous solution was extracted with ethyl acetate and freeze-dried to reveal the product (89 mg) as a white solid. $\nu_{max}$ (KBr) 1785, 1690, 1615 (br) cm$^{-1}$; δ (D$_2$O) 2.97 (1H, d, J 17 Hz, 6β-C$\underline{H}$), 3.50 (1H, dd, J 17 Hz, J' 2.5 Hz, 6α-C$\underline{H}$), 3.60 (2$\overline{H}$, d, J 6 Hz, OC$\underline{H_2}$-CHO$\overline{H}$), 4.12 (2H, d, J 8 Hz, 9-CH$_2$), 4.76 [2H, m, consists of 1H, 8-C$\underline{H}$ and 1H, CH$_2$C$\underline{H}$OH; multiplet partially obscured by HDO peak], 4.92 (1H, br.s, 3-C$\underline{H}$), 5.67 (1H, d, J 2.5 Hz, 5-C$\underline{H}$), 7.35 (5h, s, Ph).

EXAMPLE 48

Preparation of Methyl 9-O-[(2'-hydroxy-2'-phenyl)ethyl]clavulanate

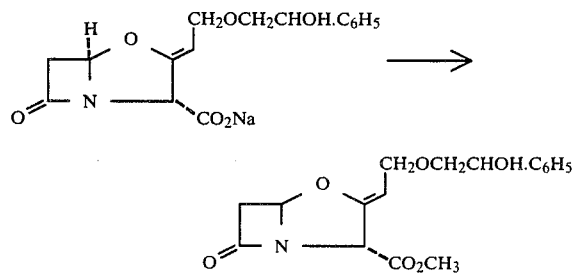

The sodium salt (50 mg) was dissolved in DMF (3 ml) and stirred at room temperature with methyl iodide (0.8 ml) for 4 hours. The DMF was removed on a rotary evaporator, under reduced pressure. The residue was partitioned between ethyl acetate and water. The ethyl acetate solution was washed, several times, with water, dried over Na$_2$SO$_4$, filtered, and evaporated. Yield 23 mg; $\nu_{max}$ (CHCl$_3$) 3600, 1800, 1745, 1705 cm$^{-1}$; m.w. (mass spectroscopy) 333.

EXAMPLE 49

Preparation of methoxymethyl O-ethylclavulanate

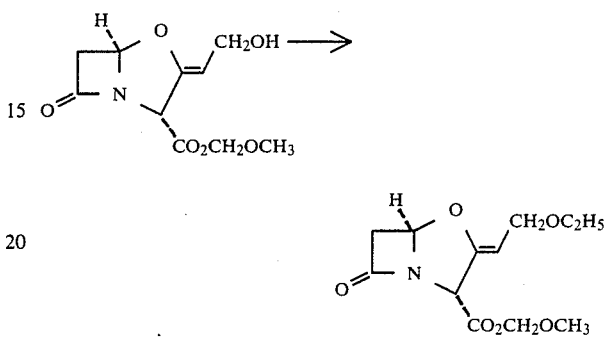

Methoxymethyl clavulanate (2.43 g, 0.01 mole), sodium carbonate anhydrous (4 g, large excess) and triethyloxonium tetrafluoroborate (5.7 g, 0.03 mole) in dry dichloromethane (125 ml) at $-30°$ C. were stirred vigorously. The mixture was allowed to warm up to room temperature during 1 hour, then stirred for 4 hours. The reaction was followed by tlc. Water (20 ml) was added, agitated, and separated. The solvent layer was dried over sodium sulphate, filtered and evaporated to a pale yellow oil. This was subjected to column chromatography over silica gel, eluting with ethyl acetate-methylcyclopentane, (1:3) then with ethyl acetate and cyclohexane graded from 2:1 to pure ethyl acetate. The first eluted product was the title compound (1.5 g) followed by a small amount of unreacted starting material (0.1 g).

I.r. (film) 1805 (β-lactam C=O) 1755 (ester C=O) 1700 (C=C)

n.m.r. (CDCl$_3$) 1.18 (3H, t, J 7 Hz, C$\underline{H_3}$CH$_2$) 3.02 (1H, d, J 17 Hz, 6-β-C$\underline{H}$) 3.42 (2H, q, J 7 Hz, CH$_3$C$\underline{H_2}$) 3.44 (1H, dd, J 17 and 3 Hz, 6-α-CH) 3.45 (3H, s, OC$\underline{H_3}$) 4.04 (2H, d, J 7 Hz, C$\underline{H_2}$—CH=) 4.86 (1H, bt, J 7 Hz, C$\underline{H_2}$—CH=) 5.04 (1H, bs, 3-C$\underline{H}$) 5.23, 5.30 (2$\overline{H}$, ABq, J 5 Hz, OC$\underline{H_2}$O) 5.65 δ (1H, d, J 3 Hz, 5-C$\underline{H}$).

The corresponding methoxymethyl O-methylclavulanate may be made in like manner.

(The starting material may be prepared by the reaction of sodium clavulanate and methyoxymethyl chloride in dimethylformamide in conventional manner).

EXAMPLE 50

Preparation of lithium O-ethylclavulanate

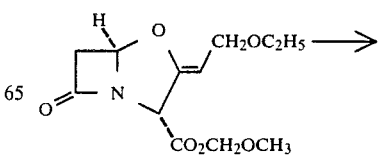

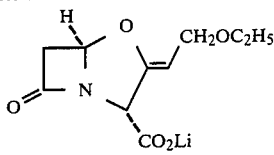

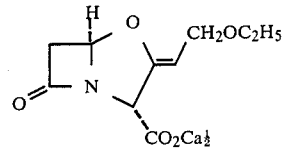

Methoxymethyl O-ethylclavulanate (0.5 g) in tetrahydrofuran (5 ml) was added to water (25 ml). The mixture was maintained at pH 8.5–9.0 by the addition of 1.0 ml lithium hydroxide solution using a "Metrohm" pH-Stat (1.8 ml required). The aqueous solution was evaporated to dryness in vacuo and triturated with acetone to yield a pale yellow crystalline solid, which was collected, washed with ether and air-dried, to yield 0.25 g of the title compound. It had the following properties:

I.r. (Nujol mull) 1785 ($\beta$-lactam C=O) 1685 (C=C) 1615 cm$^{-1}$ (—CO$_2^-$)

n.m.r. (in D$_2$O) 1.11 (3H, t, J 7 Hz, CH$_2$CH$_3$) 3.05 (1H, d, J 17 Hz, 6-$\beta$-CH) 3.48 (2H, q, J 7 Hz, CH$_2$CH$_3$) 3.50 (1H, dd, J 17 Hz, and 3 Hz, 6-$\alpha$-CH) 4.04 (2H, d, J 7 Hz, CH$_2$—CH=) 4.82 (1H, t, J 7 Hz, CH=) 4.88 (1H, s, 3-CH) 5.65 $\delta$ (1H, d, J 3 Hz, 5-CH).

The corresponding lithium salt of O-methylclavulanate may be obtained in like manner.

EXAMPLE 51

Preparation of sodium O-ethylclavulanate

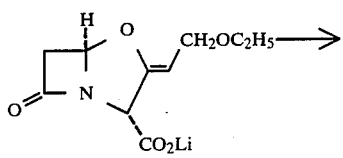

Lithium O-ethylclavulanate (0.25 g) in water (2 ml) was passed through a bed of "Amberlite" 1R 120 (Standard grade) (Na$^+$ form) (8 ml wet resin). The eluate was collected, and evaporated to dryness in vacuo. The residue was treated with acetone-ether (1:1, 5 mls), filtered off, washed with ether and air-dried, to yield 0.17 g of sodium O-ethylclavulanate as a free flowing colourless powder. (The product appeared crystalline under polarised light).

EXAMPLE 52

Calcium O-ethylclavulanate

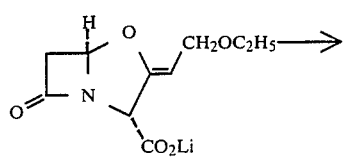

A solution of lithium O-ethylclavulanate (0.15 g) in water (3 ml) was applied to the top of a column of Amberlite IR 120 (Ca$^{2+}$ form; 25 ml of wet resin). The column was eluted with water until the product started to appear in the eluate (as shown by striations) and then 10 ml of eluate was collected. The solution was evaporated in vacuo to a pale yellow syrup. To this syrup was added acetonitrile (10 ml) and the solution re-evaporated and iso-propanol (10 ml) was added to the residue and this solution was evaporated to yield a foam. This foam was triturated with ether (10 ml) to yield a pale cream-coloured solid which was filtered off, washed with ether and air dried to yield calcium O-ethylclavulanate as a free-flowing powder (0.12 g).

(The calcium salt of the resin was prepared by passing a saturated solution of calcium hydroxide solution upwards through the bed of resin until the effluent was strongly alkaline. The resin was then washed with distilled water until the effluent was neutral).

The calcium O-ethylclavulanate may also be prepared from the sodium salt in like manner.

Calcium O-methylclavulanate may also be prepared by such processes.

EXAMPLE 53

Potassium O-methylclavulanate

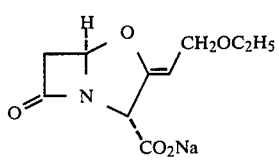

A mixture of benzyl 9-O-methylclavulanate (0.5 g) and potassium bicarbonate (0.165 g) in tetrahydrofuran-water (5:1, 12 ml) was hydrogenated at room temperature and pressure for 0.5 h in the presence of 10% palladium-charcoal (0.16 g). The mixture was then filtered and the filtrate evaporated to give the title compound as a brownish hygroscopic gum. This was dissolved in acetone (5 ml) and precipitated with ether to give a light brown powder (0.25 g).

EXAMPLE 54

Pharmaceutical Compositions a. Sterile sodium O-methylclavulanate (50 mg) may be dissolved in sterile water-for-injection (1 ml) and the resulting solution administered by injection.

b. Sterile sodium O-methylclavulanate (50 mg) may be dissolved in sterile water-for-injection (0.5 ml) and mixed with a solution of sterile sodium amoxycillin (250 mg) in sterile water-for-injection (0.5 ml). The resulting solution may be used for immediate administration by injection.

EXAMPLE 55

Potassium O-ethylclavulanate

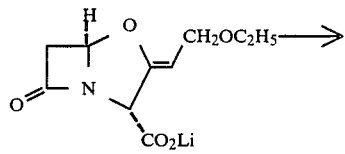

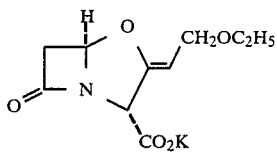

A solution of lithium O-ethylclavulanate (2.5 g) in water (20 ml were percolated down a column of Amberlite IR 120 K+ form (100 ml of wet resin) and washed slowly through with distilled water. The effluent containing the potassium salt (detected by t.l.c. and potassium permanganate spray) were combined (total volume approx. 200 ml) and freeze-dried to yield a somewhat-impure preparation of potassium O-ethylclavulanate (1.6 g). Part of this material (500 mg) was dissolved in ethanol (5 ml) and decolourised with charcoal and precipitated with ether (50 ml) to give 260 mg of solid which was shown to be of good purity by n.m.r. and i.r.

Elemental analysis: N=5.2%, C=43.8%, H=4.9%, K=14.4% [$C_{10}H_{12}NO_5K$ requires N=5.3%, C=45.2%, H=4.6%, K=14.7%]

EXAMPLE 56

Benzyl 9-O-(2-propyl)clavulanate

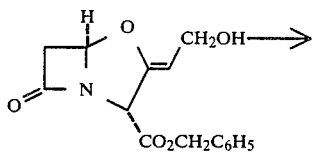

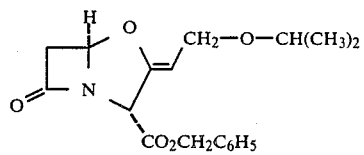

The process used for the preparation of the title compound (0.47 g) was as described in Example 42 replacing the iodobutane with 2-iodopropane (5 ml).

I.r. 1805, 1750 1698 cm$^{-1}$.

N.m.r. (CDCl$_3$)δ: 1.10 (6H, d, J 7 Hz), 2.96 (1H, d, J 17 Hz), 3.40 (1H, dd, J 17 Hz and 3 Hz), 3.51 (1H, dq, J 7 Hz), 3.80–4.30 (2H, m), 4.77 (1H, t, J 7 Hz), 5.02 (1H, s), 5.13 (2H, s), 5.59 (1H, d, J 3 Hz), 7.26 (5H, s).

EXAMPLE 57

Lithium 9-O-(2-propyl)clavulanate

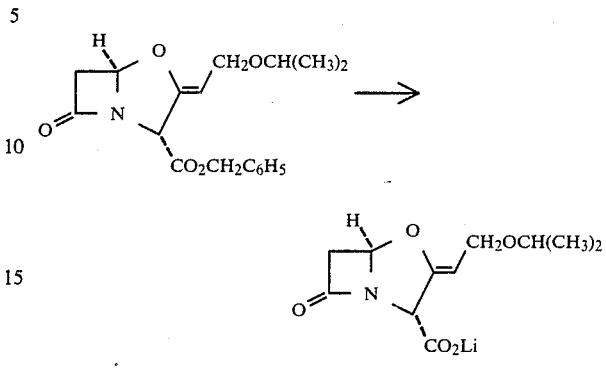

Benzyl 9-O-(2-propyl)clavulanate (0.47 g) in tetrahydrofuran (25 ml) containing water (0.1 ml) and 10% palladised charcoal (0.23 g), was hydrogenated at ambient temperature and pressure for 20 minutes. Treatment of this solution by the method of Example 56 yield the lithium salt as a colourless crystalline solid (0.2 g).

I.r. 1770, 1700, 1620 cm$^{-1}$.

EXAMPLE 58

Lithium 9-O-(2-butyl)clavulanate (DL)

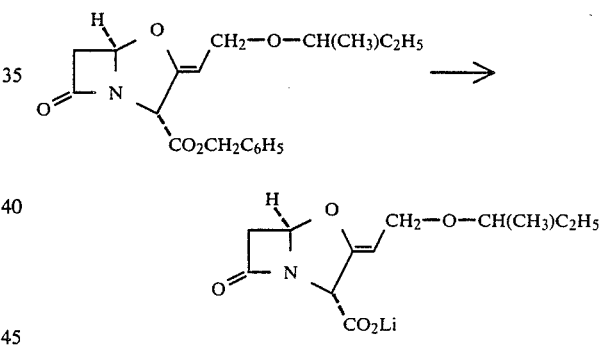

A solution of benzyl 9-O-(2-butyl)clavulanate (1 g) in tetrahydrofuran (50 ml) and water (0.2 ml) was hydrogenated over 10% palladised charcoal for 20 mins at ambient temperature and pressure. (At this time tlc showed a trace of ester unreacted). The catalyst was removed by filtration through a bed of kieselguhr, washed through with a little tetrahydrofuran (5 ml) and the filtrate diluted with water (150 ml). The solution was titrated to a pH of 7.1 with 1.0M lithium hydroxide, then evaporated to a pale yellow solid in vacuo. This was titrated with acetone (10 ml), filtered off, washed with ether (10 ml) and dried in air, to yield the product (0.28 g) as an off-white solid.

I.r. 1620, 1695 1770 with shoulder at 1785 cm$^{-1}$.

N.m.r. D$_2$O δ 0.73 (3H, t, J 7 Hz), 9.01 (3H, d, J Hz), 1.36 (2H, pentuplet, J 7 Hz), 2.96 (1H, d, J 17 Hz), 3.41 (1H, sextuplet, J 7 Hz), 3.45 (1H, dd, J 17 Hz, 3Hz), 4.01 (2H, d, J 7 Hz), 4.77 (1H, t, J 7 Hz), 4.83 (1H, s), 5.61 (1H, d, J 3 Hz).

EXAMPLE 59

Lithium 9-O-tert-amylclavulanate

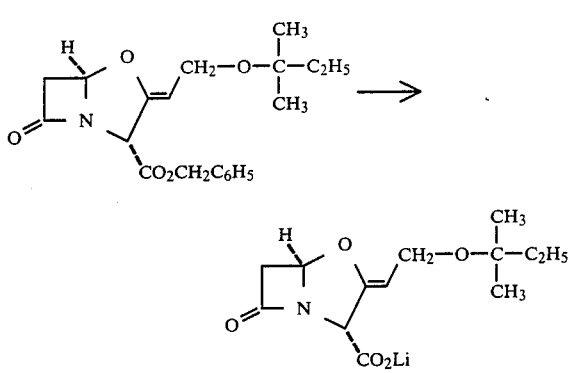

Benzyl O-tert-amylclavulanate (0.43 g) in tetrahydrofuran (25 ml) containing water (0.1 ml) was hydrogenated over 10% palladised charcoal (0.22 g) for 20 mins at ambient temperature and presure, when tlc showed no benzyl ester remaining. The catalyst was removed by filtration, and the filtrate diluted to 100 ml with water, neutralised to pH 7.0 with 1M Li OH solution, and evaporated to near dryness in vacuo. The remaining syrup was triturated with acetone to yield a gelatinous solid, which was collected by filtration, washed with acetone and air-dried, to yield 0.18 g of the product as an off-white solid.

I.r. $-1619$, 1703, 1778 (broad) $\beta$-lactam cm$^{-1}$.

N.m.r. $D_2O\delta-0.79$ (3H, t, J 7 Hz), 1.14 (6H, bs), 1.51 (2H, q, J JHz), 3.04 (1H, d, J 17 Hz), 3.52 (1H, dd, J 17 Hz), 3.98 (2H, d, J, 7 Hz), 4.79 (1H, t, J, 7 Hz), 4.87 (1H, s), 5.67 (1H, d, J, 3 Hz).

EXAMPLE 60

Benzyl 9-O-n-butylclavulanate

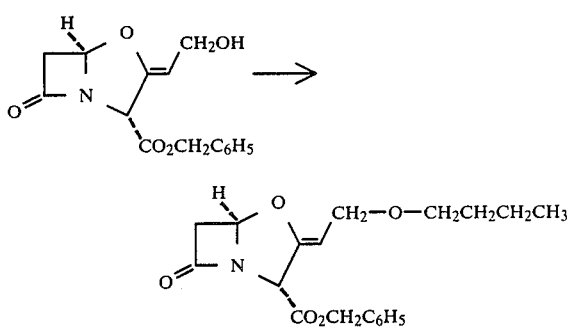

A mixture of benzyl clavulanate (2.89 g) silver oxide (4 g) calcium calcium oxide (4 g) and 1-iodobutane (5.7 ml) in ethyl acetate (7 ml) was heated and stirred under reflux for 2½ hour. At this time tlc (cyclopentanemethylacetate 2:1) showed a mixture of starting material and product. The insoluble materials were filtered off, and washed with ethyl acetate (10 ml). The filtrate was evaporated under reduced pressure to an orange oil, which was subjected to column chromatography on silica gel using cyclohexane and ethyl acetate graded from 10:1 to 1:1 ratio as eluents. Fractions containing the ether (by tlc) were collected, combined, and evaporated to a pale yellow oil under reduced pressure, to yield 0.34 g pure ether and 0.4 g slightly less pure material.

I.r. 1805, 1750, 1695 cm$^{-1}$.

N.m.r. (CDCl$_3$)$\delta$: 0.90 (3H, t, J 6.5 Hz, CH$_2$CH$_3$), 1.12–1.70 (4H, m, (CH$_2$)$_2$CH$_3$), 2.99 (1H, d, J 17 Hz, 6-$\beta$-CH), 3.33 (2H, t, J 6.5 Hz, OCH$_2$CH$_2$) 3.44 (1H, dd, J 17 Hz and 3 Hz, 6-$\alpha$-CH), 3.83–4.19 (2H, m, 9-CH$_2$)4.66–4.91 (1H, m, 8-CH), 5.05 (1H, s, 3-CH), 5.15 (2H, s, CH$_2$Ph), 5.63 (1H, d, J 3 Hz, 5-CH) and 7.29 (5H, s, CH$_2$C$_6$H$_5$).

The benzyl ester (0.74 g) was hydrogenated in the manner of Example 59 to yield the pure lithium salt (0.27 g) as an almost colourless crystalline solid.

EXAMPLE 61

Benzyl 9-O-n-hexylclavulanate

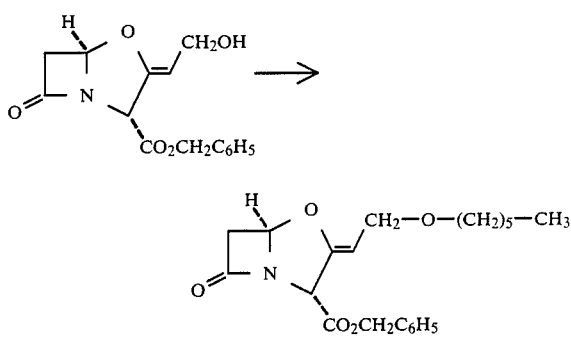

The title compound (0.4 g) was prepared as an oil by the method of Example 60 replacing the 1-iodobutane by 1-iodohexane (10.6 g).

I.r. 1805, 1757, 1698 cm$^{-1}$.

N.m.r. (CDCl$_3$)$\delta$ 0.88 (3H, t, J 6 Hz), 1.12–1.50 (8H, bm), 2.99 (1H, d, J 17 Hz) 3.32 (2H, t, J 6 Hz), 3.43 (1H, dd, J 17 and 3 Hz), 4.02 (2H, d, J 7 Hz), 4.79 (1H, t, J 7 Hz), 5.05 (1H, s), 5.15 (2H, s), 5.64 (1H, bs) and 7.29 (5H, s).

Using the method of Example 56 the ester (0.4 g) was converted to the crystalline lithium salt (0.12 g).

I.r. 1775, 1698, 1622 cm$^{-1}$.

EXAMPLE 62

Biological Data

| a. Blood levels in mice after sub-cutaneous administration of 50 mg/kg of a solution of sodium O—methylclavulanate | | | | | | | |
|---|---|---|---|---|---|---|---|
| Compound | Mean Result | 10 min | 20 min | 30 min | 45 min | 60 min | 90 min |
| Sodium O—methylclavulanate | for 5 mice | 14.5 | 12.8 | 7.9 | 4.1 | 1.4 | 0.48 |
| Sodium clavulanate | for 5 mice | 9.3 | 8.7 | 2.99 | 1.95 | 0.5 | 0.09 |

| b. Blood levels in mice after oral administration of 20 mg/kg of sodium O—methylclavulanate | | | | | |
|---|---|---|---|---|---|
| Time | 15 min | 30 min | 45 min | 60 min | 90 min |
| µg/ml | 5.2 | 3.4 | 2.2 | 1.2 | 0.5 | c. MIC values of ampicillin alone and together with sodium O-methylclavulanate against 3 strains of *Straphylococcus aureus* and 3 strains of R+ E. coli

| μg/ml of sodium O—methyl clavulanate | Staph. Russell | Staph. H | Staph. M B9 | *E. coli* JT 39 | *E. coli* JT 68 | *E. coli* JT 98 |
|---|---|---|---|---|---|---|
| 0 | 80 | 640 | 640 | <2560 | 2560 | 1280 |
| 0.5 | 0.16 | 1.20 | 0.30 | — | — | — |
| 1.0 | 0.04 | 1.20 | 0.02 | 40 | 40 | 40 |
| 2.5 | 0.01 | 0.60 | 0.02 | 10 | 20 | 10 |
| 5.0 | 0.005 | 0.60 | <0.005 | 10 | 10 | 5 |
| 10.0 | — | — | — | 1.2 | 5 | 1.2 |

The MIC of sodium O—methylclavulanate against each test organism was in the range 20–40 μg/ml.

The MIC of sodium O-methylclavulanate against each test organism was in the range 20–40 μg/ml.

d. $CD_{50}$ values of ampicillin alone and together with sodium O-methylclavulanate against an E. coli JT 39 (R+) infection.

The test compounds were administered sub-cutaneously in freshly prepared buffered saline at 1 hour and 5 hours post intra peritoneal infection:

| | $CD_{50}$ mg/kg (x2) | | | |
|---|---|---|---|---|
| | Synergist = Sodium O—methyl-clavulanate | | Synergist = Sodium clavulanate | |
| | Test 1 | Test 2 | Test 1 | Test 2 |
| Sodium Amoxycillin alone | >1000 | | >1000 | |
| Sodium Amoxycillin + 1 mg/kg of Synergist | — | <12 | — | 81 |
| Sodium Amoxycillin + 2 mg/kg of Synergist | 12 | 4 | 23 | 25 |
| Sodium Amoxycillin + 5 mg/kg of Synergist | 3.9 | — | 11.5 | — | e. $CD_{50}$ values of amoxycillin alone and together with a salt of O-ethylclavulanate acid against an E. coli JT 39 (R+) infection.

The test compounds were administered to mice subcutaneously in freshly prepared buffered saline (0.4 mg/ml) at 1 hour and 5 hours post inter peritoneal infection.

| | $CD_{50}$ mg/kg (x2) | | | |
|---|---|---|---|---|
| | Synergist = Salt of O—ethylclavulanic acid | | Synergist = Salt of clavulanic acid | |
| | Test 1 | Test 2 | Test 1 | Test 2 |
| Sodium Amoxycillin alone | >1000 | | >1000 | |
| Sodium Amoxycillin + 2 mg/kg of Synergist | 3.7 | 13.5 | 14 | — |
| Sodium Amoxycillin + 1 mg/kg of Synergist | — | 27 | — | 47 |

In a similar test dosing at 1, 3 and 5 hours post infection the following results were obtained:

| | $CD_{50}$ mg/kg (x3) | | | |
|---|---|---|---|---|
| | Synergist = Salt of O—ethylclavulanic acid | | Synergist = Salt of clavulanic acid | |
| | Test 1 | Test 2 | Test 1 | Test 2 |
| Sodium Amoxycillin alone | >1000 | | >1000 | |
| Sodium Amoxycillin + 20 mg/kg synergist | 14.6 | 27 | 7.3 | 11 |
| Sodium Amoxycillin + 10 mg/kg synergist | — | 44 | — | 16.6 | f. $CD_{50}$ values of amoxycillin alone and together with a salt of O-methylclavulanic acid or O-ethylclavulanic acid against a Klebsiella I.112 infection.

The test compounds were administered orally to mice at 1, 3 and 5 hours post inter peritoneal infection.

| | $CD_{50}$ mg/kg (x3) |
|---|---|
| Amoxycillin alone | >1000 |
| Amoxycillin + 2 mg/kg salt of O—methylclavulanic acid | 14 |
| Amoxycillin + 1 mg/kg salt of O—methylclavulanic acid | 26 |
| Amoxycillin + 2 mg/kg salt of O—ethylclavulanic acid | 14 |
| Amoxycillin + 1 mg/kg salt of O—ethylclavulanic acid | 35 |
| Amoxycillin + 1 mg/kg salt of clavulanic acid | 42 |
| Amoxycillin + 1 mg/kg salt of clavulanic acid | >50 |

[In these tests amoxycillin trihydrate equivalent to the stated weights of amoxycillin were used].

What we claim is:

1. A pharmaceutical composition for treating bacterial infections in humans and animals which comprises a synergistically effective amount of an ether of the formula (II):

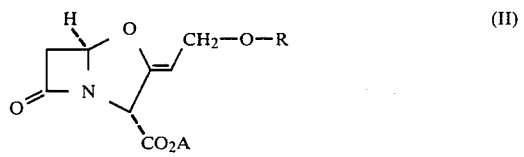

or

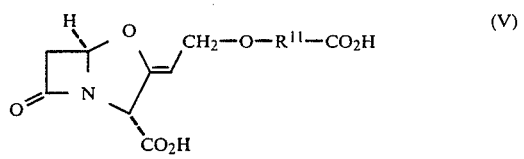

or a pharmaceutically acceptable salt or a pharmaceutically acceptable ester of a compound of the formula (V), wherein R is a hydrocarbon of up to 18 carbon atoms unsubstituted or substituted by halogen, a group of the formula $OR^1$, $OH$, $OCOR^1$, $COR^1$, $CO_2R^1$, $NR^2COR^1$, $NR^2CO_2R^1$, $SOR^1$, $SO_2R^1$, $NH_2$, $NR_1R^2$, $NO_2$, $CONR^1R^2$, carboxyl or a pharmaceutically acceptable salted carboxyl or by halogen and one of said groups, wherein $R^1$ is a hydrocarbon of up to 8 carbon atoms and $R^2$ is a hydrocarbon of up to 4 carbon atoms, or R is $CR^4R^5R^6$ wherein $R^4$ and $R^5$ are independently alkyl of up to 3 carbon atoms or phenyl unsubstituted or substituted by halogen or a group of the formula $R^7$ or $OR^7$ wherein $R^7$ is alkyl of up to 3 carbon atoms; and $R^6$ is hydrogen, alkyl of up to 3 carbon atoms or phenyl unsubstituted or substituted by halogen or a group of the formula $R^8$ or $OR^8$ wherein $R^8$ is alkyl of up to 3 carbon atoms, $R^{11}$ is a hydrocarbon of 1 to 8 carbon atoms unsubstituted or substituted by halogen, a group of the formula $OR^{12}$, $OCOR^{12}$, $COR^{12}$ or OH, or by halogen and one of said groups wherein $R^{12}$ is alkyl of 1 to 4 carbon atoms, and A is a group such that $CO_2A$ is a carboxylic acid moiety, a pharmaceutically acceptable salt or a pharmaceutically acceptable ester thereof, and an antibacterially effective amount of a penicillin, in combination with a pharmaceutically acceptable carrier.

2. A composition according to claim 1 wherein the ether is of the formula (IIa):

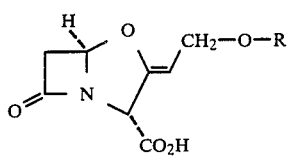

(IIa)

or a pharmaceutically acceptable salt thereof wherein R is a hydrocarbon of up to 18 carbon atoms unsubstituted or substituted by halogen, a group of the formula $OR^1$, OH, $OCOR^1$, $COR^1$, $CO_2R^1$, $NR^2COR^1$, $NR^2CO_2R^1$, $SOR^1$, $SO_2R^1$, $NH_2$, $NR^1R^2$, $NO_2$, $CONR^1R^2$, carboxyl or a pharmaceutically acceptable salted carboxyl or by halogen and one of said groups, wherein $R^1$ is a hydrocarbon of up to 8 carbon atoms and $R^2$ is a hydrocarbon of up to 4 carbon atoms; or is of the formula (IIb):

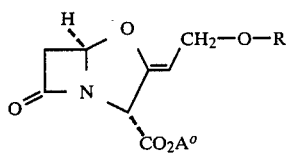

(IIb)

wherein A° is a group such that $CO_2A°$ is a pharmaceutically acceptable ester moiety and R is as above defined.

3. A composition according to claim 1 wherein R contains up to 7 carbon atoms.

4. A composition according to claim 1 wherein R is said hydrocarbon unsubstituted or substituted by halogen, a group of the formula $OR^1$, $OCOR^1$, $CO_2R^1$, carboxyl or a pharmaceutically acceptable salted carboxyl or by halogen and one of said groups wherein $R^1$ is a hydrocarbon of up to 8 carbon atoms.

5. A composition according to claim 1 wherein $R^1$ is alkyl of 1 to 4 carbon atoms, phenyl or benzyl.

6. A composition according to claim 1 wherein one or both of $R^1$ and $R^2$ are methyl.

7. A composition according to claim 1 wherein R is $CH_2R^9$ wherein $R^9$ is naphthyl, phenyl or phenyl substituted by halogen or a group $R^{10}$ or $OR^{10}$ wherein $R^{10}$ is alkyl of up to 3 carbon atoms.

8. A composition according to claim 1 wherein A is hydrogen or a sodium, potassium, calcium, magnesium, ammonium, monoalkyl ammonium, dialkyl ammonium, trialkyl ammonium or quaternary alkyl ammonium moiety of 1 to 6 carbon atoms in each alkyl moiety.

9. A composition according to claim 1 wherein the compound is in the form of the sodium, potassium or calcium salt.

10. A composition according to claim 1 wherein the compound is in the form of a pharmaceutically acceptable ester.

11. A composition according to claim 10 wherein the compound of the formula (II) is of the formula (III) or (IV):

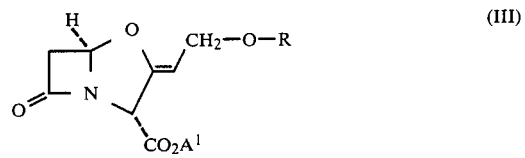

(III)

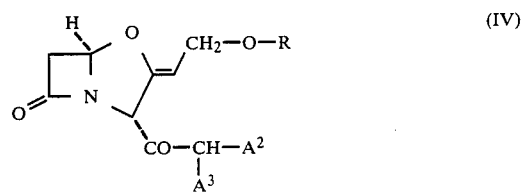

(IV)

wherein R is a hydrocarbon of up to 18 carbon atoms unsubstituted or substituted by halogen, a group of the formula $OR^1$, OH, $OCOR^1$, $COR^1$, $NR^2COR^1$, $NR^2CO_2R^1$, $SOR^1$, $SO_2R^1$, $NH_2$, $NR^1R^2$, $NO_2$, $CONR^1R^2$, carboxyl or a pharmaceutically acceptable salted carboxyl or by halogen and one of said groups, wherein $R^1$ is a hydrocarbon of up to 8 carbon atoms and $R^2$ is a hydrocarbon of up to 4 carbon atoms; $A^1$ is alkyl of 1 to 8 carbon atoms unsubstituted or substituted by halogen of a group of the formula $OA^4$, $OCOA^4$, $SA^4$ or $SO_2A^4$ wherein $A^4$ is a hydrocarbon of up to 6 carbon atoms; $A^2$ is hydrogen, alkyl of up to 4 carbon atoms or phenyl unsubstituted or substituted by halogen or by a group $A^5$ or $OA^5$ wherein $A^5$ is alkyl of up to 6 carbon atoms; and $A^3$ is phenyl unsubstituted or substituted by halogen or by a group $A^5$ or $OA^5$ wherein $A^5$ is as above defined.

12. A composition according to claim 11 wherein $A^1$ is alkyl of 1 to 8 carbon atoms unsubstituted or substituted by a group of the formula $OA^4$ wherein $A^4$ is a hydrocarbon of up to 6 carbon atoms; $A^2$ is hydrogen; $A^4$ is methyl; and $A^5$ is methyl.

13. A composition according to claim 1 wherein the compound of the formula (II) is in the form of an ester wherein the ester moiety is the acetoxymethyl, α-acetoxyethyl, pivaloyloxymethyl, phthalidyl, ethoxycarbonyloxymethyl or ethoxycarbonyloxy ethyl ester.

14. A composition according to claim 1 wherein the compound of the formula (II) is in the form of the benzyl or p-methoxybenzyl ester.

15. A composition according to claim 1 wherein $R^{11}$ is alkylene of 1 to 4 carbon atoms, phenylene or alkylene of 1 to 2 carbon atoms substituted by phenyl or phenylene.

16. A composition according to claim 1 wherein $R^{11}$ is —$CH_2$— or —$CH_2CH_2$—.

17. A composition according to claim 1 wherein the compound of the formula (II) is of the formula (VI), (VII), (VIII), (IX), (X), (XIa) or (XIb):

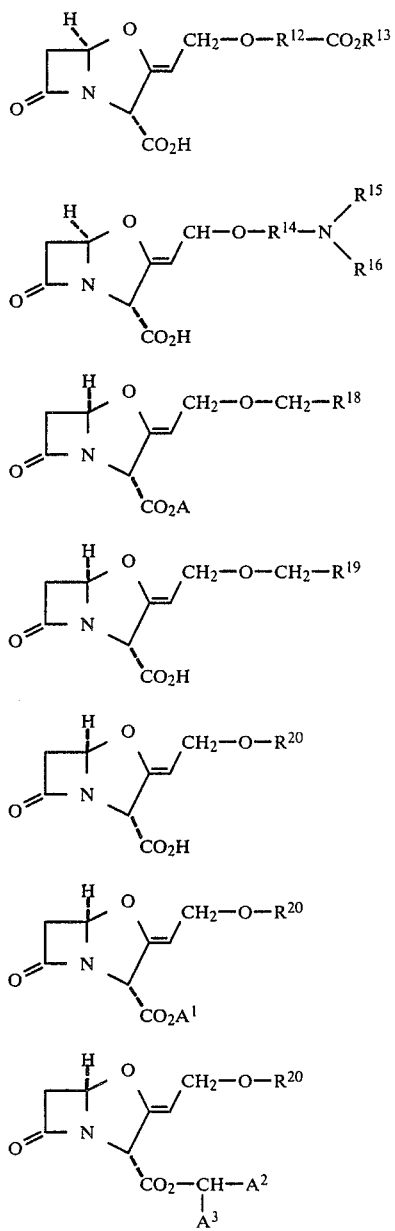

or a pharmaceutically acceptable salt or pharmaceutically acceptable ester thereof wherein $R^{12}$ is alkylene of 1 to 4 carbon atoms; $R^{13}$ is hydrogen or alkyl of 1 to 4 carbon atoms unsubstituted or substituted by phenyl; $R^{14}$ is a divalent hydrocarbon of 2 to 8 carbon atoms; $R^{15}$ is hydrogen or alkyl of 1 to 4 carbon atoms; $R^{16}$ is hydrogen, $R^{17}$, $COR^{17}$ or $CO_2R^{17}$ wherein $R^{17}$ is alkyl of 1 to 4 carbon atoms unsubstituted or substituted by phenyl; A is a group such that $CO_2A$ is a carboxylic acid moiety or a pharmaceutically acceptable salt or pharmaceutically acceptable ester thereof; $R^{18}$ is a moiety such that $CH_2R^{18}$ is an inert hydrocarbon of up to 18 carbon atoms unsubstituted or substituted by halogen, a group of the formula $OR^1$, OH, $OCOR^1$, $COR^1$, $CO_2R^1$, $NR^2COR^1$, $NR^2CO_2R^1$, $SOR^1$, $SO_2R^1$, $NH_2$, $NR^1R^2$, $NO_2$, $COHR^1R^2$, carboxyl or a pharmaceutically acceptable salted carboxyl or by halogen and one of said groups wherein $R^1$ is a hydrocarbon of up to 8 carbon atoms and $R^2$ is a hydrocarbon of up to 4 carbon atoms; $R^{19}$ is alkyl of 1 to 4 carbon atoms or phenyl unsubstituted or substituted by a carboxylic acid group, a pharmaceutically acceptable carboxyl salt, a carboxylic acid alkyl ester moiety of 1 to 4 carbon atoms in the alkyl moiety or $R^{19}$ is a carboxylic acid group, a pharmaceutically acceptable carboxyl salt or a carboxylic acid alkyl ester of 1 to 4 carbon atoms in the alkyl ester moiety; $R^{20}$ is alkyl of 1 to 5 carbon atoms; $A^1$ is alkyl of 1 to 8 carbon atoms unsubstituted or substituted by halogen or a group of the formula $OA^4$, $OCOA^4$, $SA^4$ or $SO_2A^4$ wherein $A^4$ is a hydrocarbon of up to 6 carbon atoms; $A^2$ is hydrogen, alkyl of up to 4 carbon atoms or phenyl unsubstituted or substituted by halogen or by a group $A^5$ or $OA^5$ wherein $A^5$ is alkyl of up to 6 carbon atoms; and $A^3$ is phenyl unsubstituted or substituted by halogen or by a group $A^5$ or $OA^5$ wherein $A^5$ is as above defined.

18. A composition according to claim 17 wherein $R^{12}$ is —$CH_2$— or —$CH_2CH_2$—; $R^{14}$ is alkylene or 2 to 4 carbon atoms, phenylene or alkylene of 2 to 4 carbon atoms substituted by phenyl or phenylene; $R^{20}$ is a group $CH_2R^{21}$ wherein $R^{21}$ is hydrogen or alkyl of 1 to 4 carbon atoms.

19. A composition according to claim 17 wherein the compound of the formula (VI) is in the form of a pharmaceutically acceptable salt and the compound of the formula (IX) is in the form of the sodium, potassium or calcium salt.

20. A composition according to claim 18 wherein $R^{20}$ is methyl, ethyl, n-propyl, iso-propyl, n-butyl, iso-butyl, sec-butyl or t-butyl.

21. A composition according to claim 20 wherein $R^{20}$ is methyl or ethyl.

22. A composition according to claim 17 wherein the compound of the formula (XIa) is in the form of methoxymethyl ester.

23. A composition according to claim 1 wherein the penicillin is benzylpenicillin, phenoxymethylpenicillin, carbenicillin, azidocillin, propicillin, ampicillin, amoxycillin, epicillin, ticarcillin, cyclacillin, a pharmaceutically acceptable salt thereof or a pharmaceutically acceptable ester thereof.

24. A composition according to claim 1 wherein the compound is of the formula

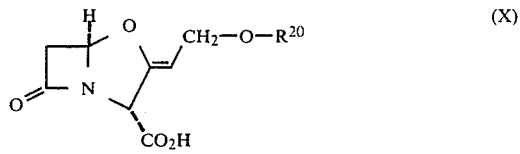

wherein $R^{20}$ is methyl and the penicillin is amoxycillin.

25. A method of treating bacterial infections in humans and animals which comprises administering to a human or animal in need thereof a synergistically effective amount of an ether of the formula (II):

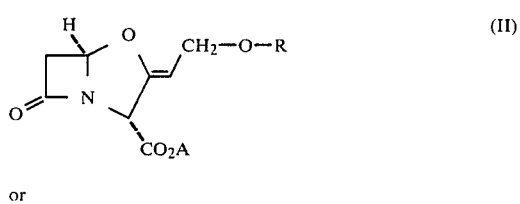

or

-continued

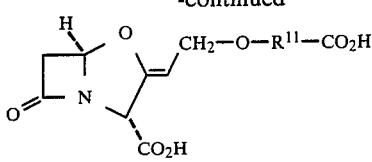
(V)

or a pharmaceutically acceptable salt or a pharmaceutically acceptable este of a compound of the formula (V), wherein R is a hydrocarbon of up to 18 carbon atoms unsubstituted or substituted by halogen, a group of the formula $OR^1$, OH, $OCOR^1$, $COR^1$, $CO_2R^1$, $NR^2COR^1$, $NR^2CO_2R^1$, $SOR^1$, $SO_2R^1$, $NH_2$, $NR_1R^2$, $NO_2$, $CONR^1R^2$, carboxyl or a pharmaceutically acceptable salted carboxyl or by halogen and one of said groups, wherein $R^1$ is a hydrocarbon of up to 8 carbon atoms and $R^2$ is a hydrocarbon of up to 4 carbon atoms, or R is $CR^4R^5R^6$ wherein $R^4$ and $R^5$ are independently alkyl of up to 3 carbon atoms or phenyl unsubstituted or substituted by halogen or a group of the formula $R^7$ or $OR^7$ wherein $R^7$ is alkyl of up to 3 carbon atoms; and $R^6$ is hydrogen, alkyl of up to 3 carbon atoms or phenyl unsubstituted or substituted by halogen or a group of the formula $R^8$ or $OR^8$ wherein $R^8$ is alkyl of up to 3 carbon atoms, $R^{11}$ is a hydrocarbon of 1 to 8 carbon atoms unsubstituted or substituted by halogen, a group of the formula $OR^{12}$, $OCOR^{12}$, $COR^{12}$ or OH, or by halogen and one of said groups wherein $R^{12}$ is alkyl of 1 to 4 carbon atoms, and A is a group such that $CO_2A$ is a carboxylic acid moiety, a pharmaceutically acceptable salt or a pharmaceutically acceptable ester thereof, and an antibacterially effective amount of a penicillin, in combination with a pharmaceutically acceptable carrier.

26. A method according to claim 25 wherein the ether is of the formula (IIa):

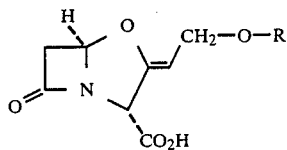
(IIa)

or a pharmaceutically acceptable salt thereof wherein R is a hydrocarbon of up to 18 carbon atoms unsubstituted or substituted by halogen, a group of the formula $OR^1$, OH, $OCOR^1$, $COR^1$, $CO_2R^1$, $NR^2COR^1$, $NR^2CO_2R^1$, $SOR^1$, $SO_2R^1$, $NH_2$, $NR^1R^2$, $NO_2$, $CONR^1R^2$, carboxyl or a pharmaceutically acceptable salted carboxyl or by halogen and one of said groups, wherein $R^1$ is a hydrocarbon of up to 8 carbon atoms and $R^2$ is a hydrocarbon of up to 4 carbon atoms; or is of the formula (IIb):

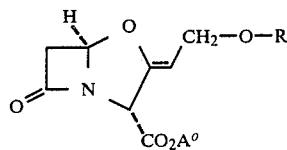
(IIb)

wherein A° is a group such that $CO_2A°$ is a pharmaceutically acceptable ester moiety and R is as above defined.

27. A method according to claim 25 wherein R contains up to 7 carbon atoms.

28. A method according to claim 25 wherein R is said hydrocarbon unsubstituted or substituted by halogen, a group of the formula $OR^1$, $OCOR^1$, $CO_2R^1$, carboxyl or a pharmaceutically acceptable salted carboxyl or by halogen and one of said groups wherein $R^1$ is a hydrocarbon of up to 8 carbon atoms.

29. A method according to claim 25 wherein $R^1$ is alkyl of 1 to 4 carbon atoms, phenyl or benzyl.

30. A method according to claim 25 wherein one or both of $R^1$ and $R^2$ are methyl.

31. A method according to claim 25 wherein R is $CH_2R^9$ wherein $R^9$ is naphthyl, phenyl or phenyl substituted by halogen or a group $R^{10}$ or $OR^{10}$ wherein $R^{10}$ is alkyl of up to 3 carbon atoms.

32. A method according to claim 25 wherein A is hydrogen or a sodium, potassium, calcium, magnesium, ammonium, monoalkyl ammonium, dialkyl ammonium, trialkyl ammonium or quaternary alkyl ammonium moiety of 1 to 6 carbon atoms in each alkyl moiety.

33. A method according to claim 25 wherein the compound is in the form of the sodium, potassium or calcium salt.

34. A method according to claim 25 wherein the compound is in the form of a pharmaceutically acceptable ester.

35. A method according to claim 34 wherein the compound of the formula (II) is of the formula (III) or (IV):

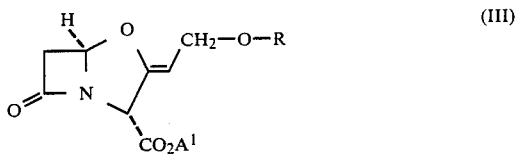
(III)

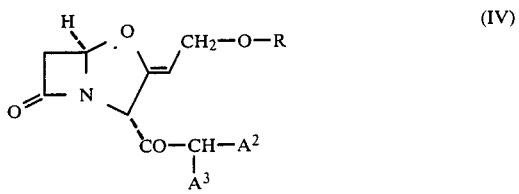
(IV)

wherein R is a hydrocarbon of up to 18 carbon atoms unsubstituted or substituted by halogen, a group of the formula $OR^1$, OH, $OCOR^1$, $COR^1$, $NR^2COR^1$, $NR^2CO_2R^1$, $SOR^1$, $SO_2R^1$, $NH_2$, $NR^1R^2$, $NO_2$, $CONR^1R^2$, carboxyl or a pharmaceutically acceptable salted carboxyl or by halogen and one of said groups, wherein $R^1$ is a hydrocarbon of up to 8 carbon atoms and $R^2$ is a hydrocarbon of up to 4 carbon atoms; $A^1$ is alkyl of 1 to 8 carbon atoms unsubstituted or substituted by halogen or a group of the formula $OA^4$, $OCOA^4$, $SA^4$ or $SO_2A^4$ wherein $A^4$ is a hydrocarbon of up to 6 carbon atoms; $A^2$ is hydrogen, alkyl of up to 4 carbon atoms or phenyl unsubstituted or substituted by halogen or by a group $A^5$ or $OA^5$ wherein $A^5$ is alkyl of up to 6 carbon atoms; and $A^3$ is phenyl unsubstituted or substituted by halogen or by a group $A^5$ or $OA^5$ wherein $A^5$ is as above defined.

36. A method according to claim 35 wherein $A^1$ is alkyl of 1 to 8 carbon atoms unsubstituted or substituted by a group of the formula $OA^4$ wherein $A^4$ is a hydrocarbon of up to 6 carbon atoms; $A^2$ is hydrogen; $A^4$ is methyl; and $A^5$ is methyl.

37. A method according to claim 25 wherein the compound of the formula (II) is in the form of an ester wherein the ester moiety is the acetoxymethyl, α-acetoxyethyl, pivaloyloxymethyl, phthalidyl, ethoxycarbonyloxymethyl or ethoxycarbonyloxy ethyl ester.

38. A method according to claim 25 wherein the compound of the formula (II) is in the form of the benzyl or p-methoxybenzyl ester.

39. A method according to claim 25 wherein $R^{11}$ is alkylene of 1 to 4 carbon atoms, phenylene or alkylene of 1 to 2 carbon atoms substituted by phenyl or phenylene.

40. A method according to claim 25 wherein $R^{11}$ is —$CH_2$— or —$CH_2CH_2$—.

41. A method according to claim 25 wherein the compound of the formula (II) is of the formula (VI), (VII), (VIII), (IX), (X), (XIa) or (XIb):

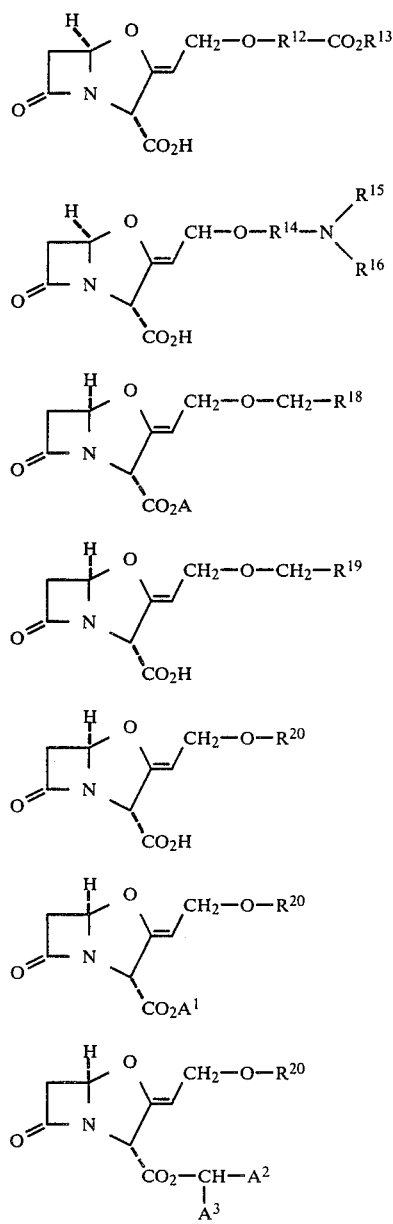

or a pharmaceutically acceptable salt or pharmaceutically acceptable ester thereof wherein $R^{12}$ is alkylene of 1 to 4 carbon atoms; $R^{13}$ is hydrogen or alkyl of 1 to 4 carbon atoms unsubstituted or substituted by phenyl; $R^{14}$ is a divalent hydrocarbon of 2 to 8 carbon atoms; $R^{15}$ is hydrogen or alkyl of 1 to 4 carbon atoms; $R^{16}$ is hydrogen, $R^{17}$, $COR^{17}$ or $CO_2R^{17}$ wherein $R^{17}$ is alkyl of 1 to 4 carbon atoms unsubstituted or substituted by phenyl; A is a group such that $CO_2A$ is a carboxylic acid moiety or a pharmaceutically acceptable salt or pharmaceutically acceptable ester thereof; $R^{18}$ is a moiety such that $CH_2R^{18}$ is an inert hydrocarbon of up to 18 carbon atoms unsubstituted or substituted by halogen, a group of the formula $OR^1$, OH, $OCOR^1$, $COR^1$, $CO_2R^1$, $NR^2COR^1$, $NR^2CO_2R^1$, $SOR^1$, $SO_2R^1$, $NH_2$, $NR^1R^2$, $NO_2$, $COHR^1R^2$, carboxyl or a pharmaceutically acceptable salted carboxyl or by halogen and one of said groups wherein $R^1$ is a hydrocarbon of up to 8 carbon atoms and $R^2$ is a hydrocarbon of up to 4 carbon atoms; $R^{19}$ is alkyl of 1 to 4 carbon atoms or phenyl unsubstituted or substituted by a carboxylic acid group, a pharmaceutically acceptable carboxyl salt, a carboxylic acid alkyl ester moiety of 1 to 4 carbon atoms in the alkyl moiety or $R^{19}$ is a carboxylic acid group, a pharmaceutically acceptable carboxyl salt or a carboxylic acid alkyl ester of 1 to 4 carbon atoms in the alkyl ester moiety; $R^{20}$ is alkyl of 1 to 5 carbon atoms; $A^1$ is alkyl of 1 to 8 carbon atoms unsubstituted or substituted by halogen or a group of the formula $OA^4$, $OCOA^4$, $SA^4$ or $SO_2A^4$ wherein $A^4$ is a hydrocarbon of up to 6 carbon atoms; $A^2$ is hydrogen, alkyl of up to 4 carbon atoms or phenyl unsubstituted or substituted by halogen or by a group $A^5$ or $OA^5$ wherein $A^5$ is alkyl of up to 6 carbon atoms; and $A^3$ is phenyl unsubstituted or substituted by halogen or by a group $A^5$ or $OA^5$ wherein $A^5$ is as above defined.

42. A method according to claim 41 wherein $R^{12}$ is —$CH_2$— or —$CH_2CH_2$—; $R^{14}$ is alkylene or 2 to 4 carbon atoms, phenylene or alkylene of 2 to 4 carbon atoms substituted by phenyl or phenylene; $R^{20}$ is a group $CH_2R^{21}$ wherein $R^{21}$ is hydrogen or alkyl of 1 to 4 carbon atoms.

43. A method according to claim 41 wherein the compound of the formula (VI) is in the form of a pharmaceutically acceptable salt and the compound of the formula (IX) is in the form of the sodium, potassium or calcium salt.

44. A method according to claim 42 wherein $R^{20}$ is methyl, ethyl, n-propyl, iso-propyl, n-butyl, iso-butyl, sec-butyl or t-butyl.

45. A method according to claim 44 wherein $R^{20}$ is methyl or ethyl.

46. A method according to claim 41 wherein the compound of the formula (XIa) is in the form of methoxymethyl ester.

47. A method according to claim 25 wherein the penicillin is benzylpenicillin, phenoxymethylpenicillin, carbenicillin, azidocillin, propicillin, ampicillin, amoxycillin, epicillin, ticarcillin, cyclacillin, a pharmaceutically acceptable salt thereof or a pharmaceutically acceptable ester thereof.

48. A method according to claim 25 wherein the compound is of the formula

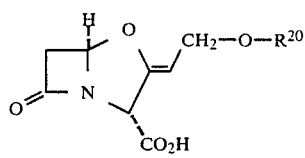

wherein $R^{20}$ is methyl and the penicillin is amoxycillin.

* * * * *